(12) United States Patent
Chi et al.

(10) Patent No.: US 8,592,585 B2
(45) Date of Patent: *Nov. 26, 2013

(54) PHOSPHORESCENT IRIDIUM COMPLEX WITH NON-CONJUGATED CYCLOMETALATED LIGANDS, SYNTHETIC METHOD OF PREPARING THE SAME AND PHOSPHORESCENT ORGANIC LIGHT EMITTING DIODE THEREOF

(75) Inventors: Yun Chi, Hsinchu (TW); Pi-Tai Chou, Taipei (TW); Yi-Hwa Song, Hsinchu (TW); Yuan-Chieh Chiu, Taoyuan County (TW); Chiung-Fang Chang, Yunlin County (TW)

(73) Assignee: National Tsing Hua University, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/219,754

(22) Filed: Aug. 29, 2011

(65) Prior Publication Data

US 2011/0313162 A1    Dec. 22, 2011

Related U.S. Application Data

(62) Division of application No. 12/000,035, filed on Dec. 7, 2007, now Pat. No. 8,030,490.

(60) Provisional application No. 60/877,603, filed on Dec. 29, 2006.

(51) Int. Cl.
    *C07F 15/00* (2006.01)
    *C07F 9/28* (2006.01)

(52) U.S. Cl.
    USPC ................................. 546/2; 546/22

(58) Field of Classification Search
    USPC ........................................................ 546/2, 22
    See application file for complete search history.

(56) References Cited

U.S. PATENT DOCUMENTS 8,288,543 B2 * 10/2012 Chi et al. .................. 546/4

FOREIGN PATENT DOCUMENTS

WO     2006098120     9/2006

* cited by examiner

*Primary Examiner* — Charanjit Aulakh
(74) *Attorney, Agent, or Firm* — Bacon & Thomas, PLLC

(57) ABSTRACT

The present invention discloses a phosphorescent tris-chelated transition metal complex comprising i) two identical non-conjugated cyclometalated ligands being incorporated into a coordination sphere thereof with a transition metal, and one ligated chromophore being incorporated into the coordination sphere; or ii) one non-conjugated cyclometalated ligand forming a coordination sphere thereof with a transition metal, and two ligated chromophores being incorporated into the coordination sphere, wherein the metal is iridium, platinum, osmium or ruthenium, and the ligated chromophore possesses a relatively lower energy gap in comparison with that of the non-conjugated cyclometalated ligand, the latter afforded an effective barrier for inhibiting the ligand-to-ligand charge transfer process, so that a subsequent radiative decay from an excited state of these transition complexes will be confined to the single ligated chromophore. The architecture and energy gap of the ligated chromophore are suitable for generation of high efficiency blue, green and even red emissions.

5 Claims, No Drawings

PHOSPHORESCENT IRIDIUM COMPLEX WITH NON-CONJUGATED CYCLOMETALATED LIGANDS, SYNTHETIC METHOD OF PREPARING THE SAME AND PHOSPHORESCENT ORGANIC LIGHT EMITTING DIODE THEREOF

This application is a divisional application of pending U.S. patent application Ser. No. 12/000,035, filed Dec. 7, 2007 (of which the entire disclosure of the pending, prior application is hereby incorporated by reference). The parent application Ser. No. 12/000,035 claims the benefit of U.S. Provisional Application No. 60/877,603, filed on Dec. 29, 2006. The disclosure of this Provisional Application is hereby incorporated by reference.

FIELD OF THE INVENTION

The present invention relates to iridium complexes, and more particularly to the phosphorescent iridium complexes with non-conjugated cyclometalated ligands, synthetic method of preparing the same and phosphorescent organic light emitting diode thereof.

BACKGROUND OF THE INVENTION

Phosphorescent organic light emitting diodes (OLEDs) are under intensive investigation because of their potential of achieving improved device brightness and performances. In contrast to the fluorescent emission, the electrophosphorescence of heavy metal complexes are easily generated from both singlet and triplet excited states and, thus, the internal quantum efficiency can reach a theoretical level of unity, rather than the 25% inherent upper limit imposed by the formation of singlet excitons for the respective fluorescent counterparts. Thus, a great deal of effort has been spent on the second and third-row transition metal complexes, for developing highly efficient phosphors that can emit all three primary colors. Despite of the elegant research on both red and green phosphors, there are only scatter reports on the room temperature blue phosphors. The best known example is one Ir(III) complex named as FIrpic in the following, which has proved to be an excellent dopant for sky-blue phosphorescent OLEDs. Further improvements were made by substituting picolinate with other ancillary ligands such as pyridyl azolate ligand to afford derivative complexes FIrpyz or FIrtaz shown in the following. These modifications have produced a hypsochromic shift of ~10 nm versus the emission of FIrpic; however, significant lowering of Q.Y. was noted in some cases, which have hampered the fabrication of the true-blue phosphorescent OLEDs.

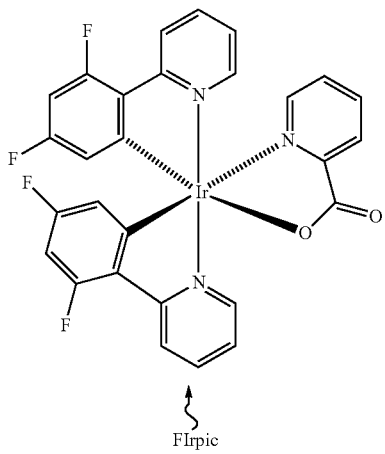

FIrpic

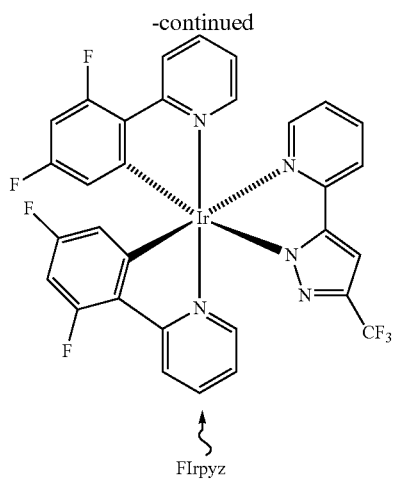

FIrpyz

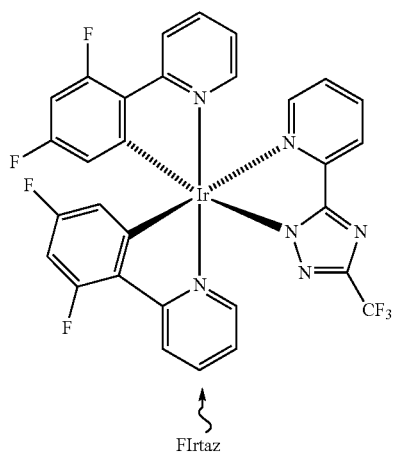

FIrtaz

In theory, one has to consider some critical design in achieving the higher efficient blue phosphorescence. One possibility is to increase the MLCT contribution in the lowest lying triplet manifold. The direct involvement of non-bonding, metal $d_\pi$ orbital enhances the coupling of the orbital angular momentums with the electron spin, such that the $T_1 \to S_0$ transition would have a large First-order spin-orbit coupling term, resulting in a drastic decrease of radiative lifetime and hence a possibility of increasing emission Q.Y. For probing such possibility, this group have prepared two isomeric, blue-emitting heteroleptic iridium (III) complexes, namely complexes (dfppy)Ir(fppz)$_2$ (complex 1 in the following) and (dfppy)Ir(fppz)$_2$ (complex 2 in the following). The contribution of MLCT character, which serves as a key factor in spin-orbit coupling enhancement, is calculated to be 27% and 17% for (dfppy)Ir(fppz)$_2$ (complex 1) and (dfppy)Ir(fppz)$_2$ (complex 2), respectively, according to the DFT calculation. As such, the respective theoretical analysis revealed an increase the $d_\pi$ contribution in (dfppy)Ir(fppz)$_2$ (complex 1) versus that of complex 2, rendering a larger First-order spin-orbit coupling term and hence shortening radiative lifetime as well as increasing the emission Q.Y., which are consistent with the experimental observations.

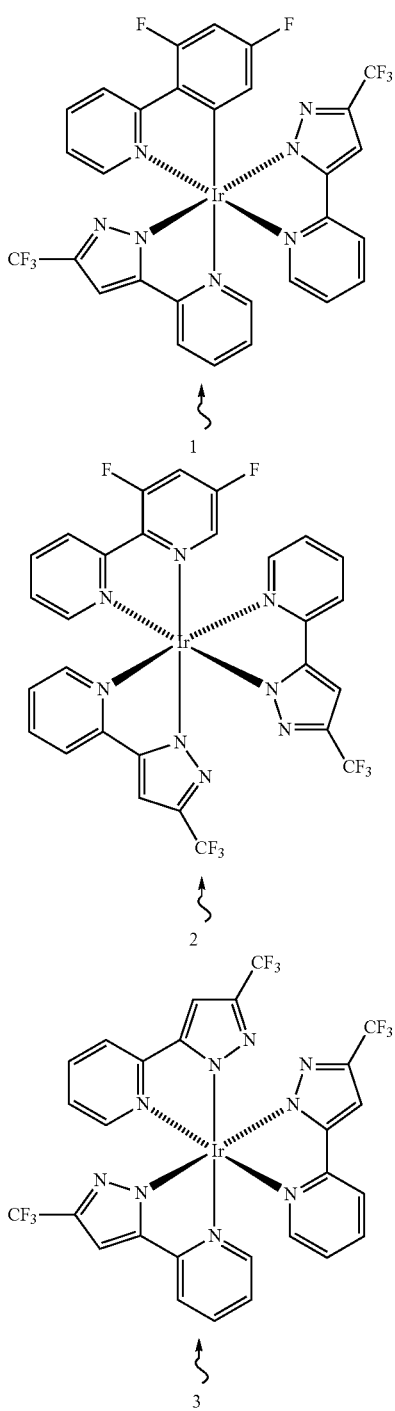

Conversely, care has taken to avoid the enhanced radiationless deactivation pathways due to the purposed enlargement of the emission band gap. One familiar deactivation pathway lies in the population to the metal-centered dd excited states, which may cause the weakness of the metal-ligand bond, resulting in a shallow potential energy surface. In an extreme case, the shallow dd potential surface may intercept with other surfaces of states and greatly channel into the radiationless deactivation. This process, however, may be minor for the third-row transition metal elements due to their strong coordination strength that far pushes up the $d_{\sigma^*}$ orbitals.

As for the third consideration, upon increasing the energy gap toward true-blue, it becomes facile for the lowest lying excited state, a state perhaps consisting of both $\pi\pi^*$ intraligand charge transfer (ILCT) and metal-to-ligand charge transfer (MLCT) in character, to mix with a thermally accessible ligand-to-ligand charge transfer (LLCT) character. Owing to its largely charge-separated character and hence partially forbidden transition probability (versus the ground state), mixing with the LLCT excited state may eventually increase the radiative lifetime, hence reduce the corresponding Q.Y. if similar deactivation mechanisms are operative. Theoretically, the participation of LLCT excited states can be suppressed by employing the facial arranged homoleptic complexes, for which the excitation is equally spread among the degenerate states of multiple chromophores. The delocalization of the electron density would not only stabilize its molecular framework but also reduce the radiationless deactivation simply due to the resulting steeper potential energy surfaces. Moreover, for the unsymmetrical meridional isomer, the three chelate ligands are located at the distinctive environment, the non-degenerated nature of these chelate molecular orbitals would then facilitate the LLCT character and giving the poor emission Q.Y. at room temperature. Such a hypothesis was confirmed by a recent investigation on the photophysical behavior of the related homoleptic complex mer-[Ir(fppz)$_3$] (complex 3 in the above), for which an unprecedented dual phosphorescence, i.e. a blue ($P_1$) and a green ($P_2$) bands deriving from the ILCT and LLCT excited states, are observed at room temperature. It is notable that the ILCT and LLCT excited states of mer-[Ir(fppz)$_3$] are nearly orthogonal to each other and possessing mainly the ligand $\pi\pi^*$ character together with a small extent (~10%) and an enhanced (20%) MLCT character, respectively. Thus, the ILCT to LLCT energy transfer, which takes place at room temperature with small barrier possibly due to certain large-amplitude motions, would also induce the rapidly quenching of the higher energy, blue phosphorescence.

SUMMARY OF THE INVENTION

The present invention provides the phosphorescent metal complexes with one or two non-conjugated cyclometalated ligands, synthetic method of preparing the same and phosphorescent organic light emitting diode thereof for blocking the occurrence of unwanted LLCT processes and possibly, giving an enhanced emission quantum yield more particularly in the much needed true-blue region.

The present invention provides the phosphorescent metal complexes with one or two non-conjugated cyclometalated ligands, synthetic method of preparing the same and phosphorescent organic light emitting diode thereof for enhancing the quantum efficiency, synthetic yield of the iridium complexes and the luminous efficiency of phosphorescent OLEDs.

In the present invention, the molecular design of phosphorescent metal complexes comprises that, for the tris-chelated transition metal complexes, if one or two exceedingly large energy-gap cyclometalated ligands were incorporated into the coordination sphere with a transition metal, the subsequent radiative decay from the excited states will be confined to the other one or two ligated chromophores that possess a slightly lowered energy gap (such as the gap for blue, green or red emission) due to the effective blocking of the ligand-to-ligand energy transfer process. Thus, this molecular design would suppress the unwanted LLCT processes, giving an enhanced emission quantum yield more particularly in the visible spectral region.

In the present invention, with the assistance of this basic designing principle and the incorporation of the chelating chromophores with a relatively lowered energy gap as well as the required rigid π-framework, the multicolor phosphorescent OLEDs doped with the metal complexes with efficient phosphorescent emission ranging from red, green and even true-blue can be successfully fabricated.

DETAILED DESCRIPTION OF THE INVENTION

Preferred embodiments of the present invention include (but not limited to) the following items:

1. A phosphorescent tris-chelated transition metal complex comprising i) two identical non-conjugated cyclometalated ligands being incorporated into a coordination sphere thereof with a transition metal, and one ligated chromophore being incorporated into the coordination sphere; or ii) one non-conjugated cyclometalated ligand forming a coordination sphere thereof with a transition metal, and two ligated chromophores being incorporated into the coordination sphere, wherein the transition metal is iridium, platinum, osmium or ruthenium, and the ligated chromophore possesses a relatively lower energy gap in comparison with that of the non-conjugated cyclometalated ligand, the latter afforded an effective barrier for inhibiting the ligand-to-ligand charge transfer process, so that a subsequent radiative decay from an excited state of these transition metal complexes will be confined to the ligated chromophore.
2. The complex of Item 1, wherein the energy gap of the ligated chromophore is for blue, green or red emission.
3. The complex of Item 1, wherein the metal is iridium.
4. The complex of Item 3, wherein the complex is represented by the following formulas Ia, Ib and their stereo isomers:

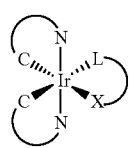

Ia

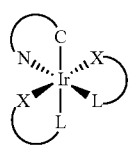

Ib wherein the non-conjugated cyclometalated ligands are represented by C and N linked with an arch, and has a formula of $Ar_1$—$C(R_1R_2)$—$Ar_2$, wherein $Ar_1$ is aromatic ring, $Ar_2$ is N-heterocyclic ring, $R_1$ and $R_2$ independently are H or methyl, wherein C in the formulas Ia and Ib is a carbon atom contained in $Ar_1$ and N in the formulas Ia and Ib is a nitrogen atom contained in $Ar_2$; the ligated chromophore is presented by the L and X linked with an arch, and has formula of $Ar_3$—$Ar_4$, wherein $Ar_3$ and $Ar_4$ independently are an aromatic ring or N-heterocyclic ring, or $Ar_3$—$Ar_4$ together are

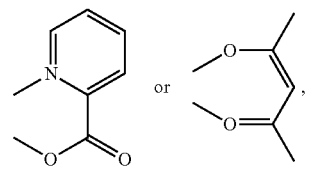

wherein L is N or O, and X is C, N or O.

5. The complex of Item 3, wherein the complex is represented by the following formulas IIa, IIb and their stereo isomers:

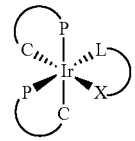

IIa

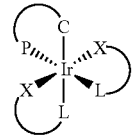

IIb wherein the non-conjugated cyclometalated ligands are represented by P and C linked with an arch, and has a formula of $Ar_5$—$C(R_1R_2)$—$P(Ar_6Ar_7)$, wherein $Ar_5$, $Ar_6$ and $Ar_7$ independently are an identical aromatic ring or different aromatic rings, $R_1$ and $R_2$ independently are H or methyl, wherein C in the formulas IIa and IIb is a carbon atom contained in $Ar_5$; the ligated chromophore is presented by the L and X linked with an arch, and has formula of $Ar_3$—$Ar_4$, wherein $Ar_3$ and $Ar_4$ independently are an aromatic ring or N-heterocyclic ring, or $Ar_3$—$Ar_4$ together are

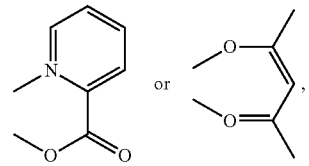

wherein L is N or O, and X is C, N or O.

6. The complex of Item 4, wherein the non-conjugated cyclometalated ligands are

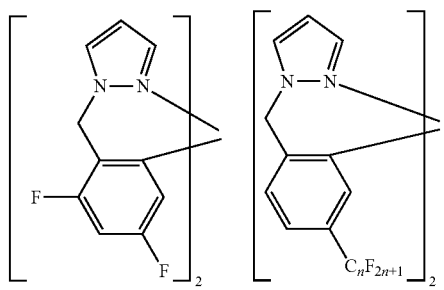

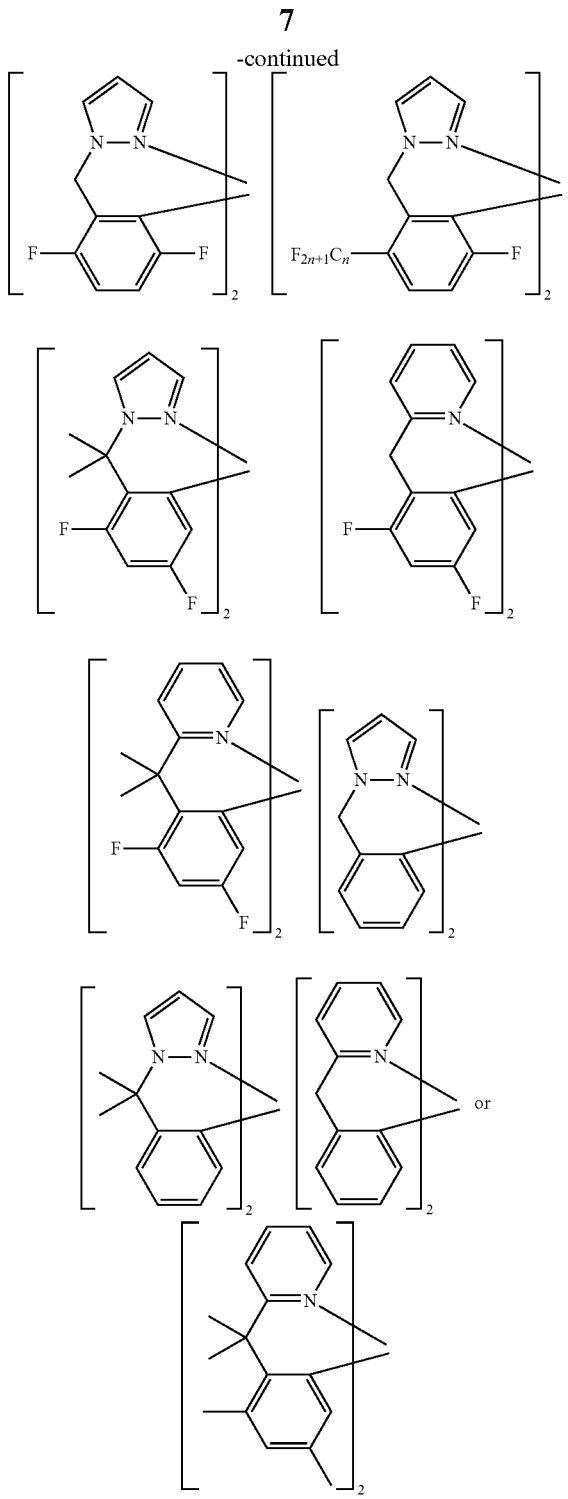

wherein n is an integer of 1-3.

7. The complex of Item 6, wherein positions of F and $C_nF_{2n+1}$ groups on phenyl rings of the non-conjugated cyclometalated ligands are varied, and n is 1.

8. The complex of Item 7, wherein F and $C_nF_{2n+1}$ groups on phenyl rings of the non-conjugated cyclometalated ligands are independently replaced by CN group.

9. The complex of Item 5, wherein the non-conjugated cyclometalated ligands are

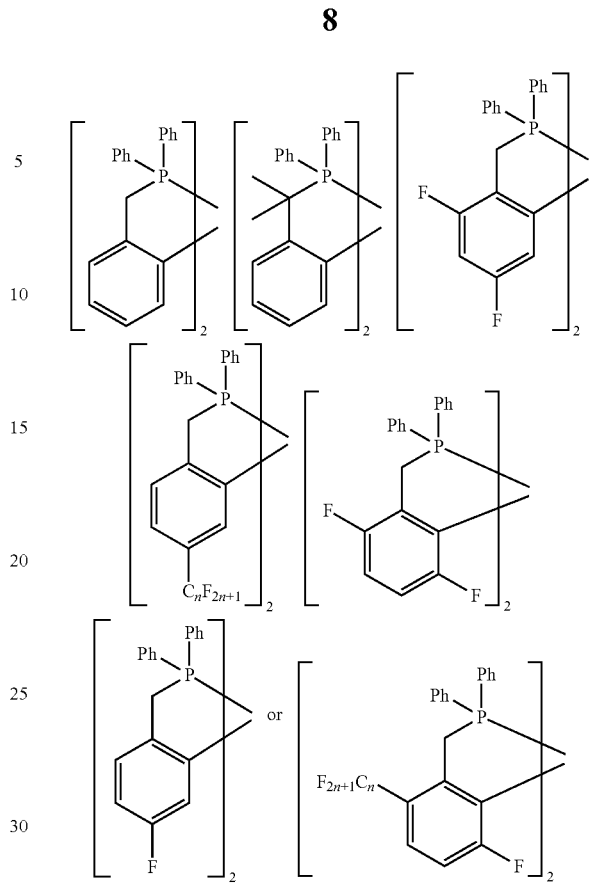

wherein Ph is phenyl, and n is an integer of 1-3.

10. The complex of Item 9, wherein positions of F and $C_nF_{2n+1}$ groups on phenyl rings of the non-conjugated cyclometalated ligands are varied, and n is 1.

11. The complex of Item 10, wherein F and $C_nF_{2n+1}$ groups on phenyl rings of the non-conjugated cyclometalated ligands are independently replaced by CN group.

12. The complex of Item 4, wherein the ligated chromophores are

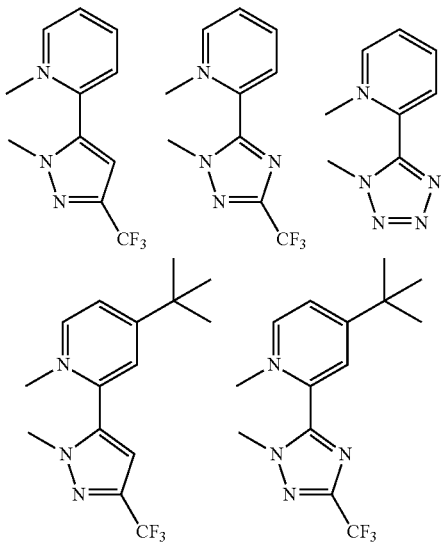

-continued

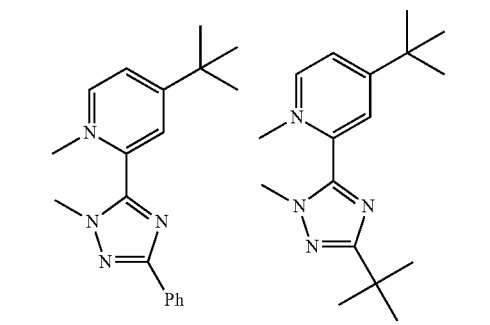

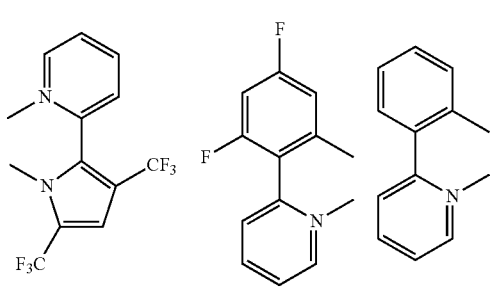

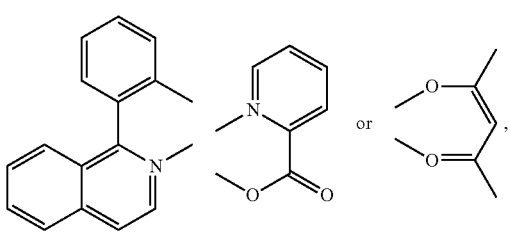

wherein Ph is phenyl.

13. The complex of Item 5, wherein the ligated chromophores are

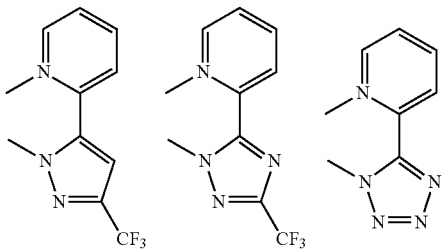

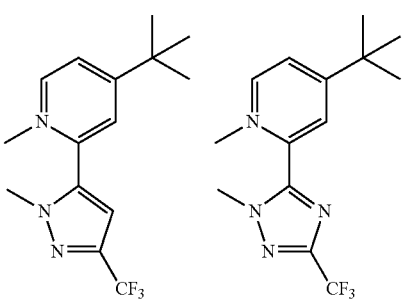

-continued

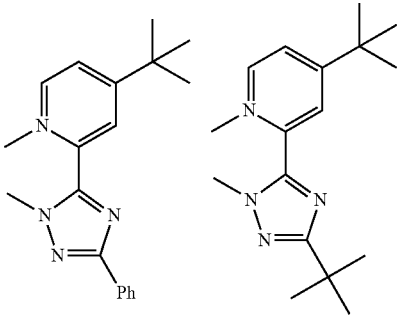

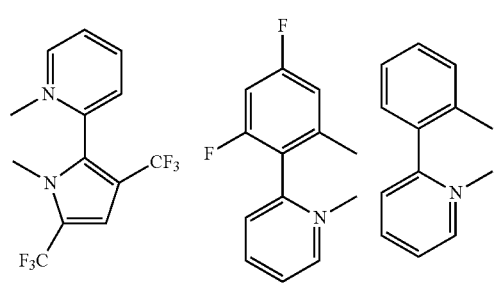

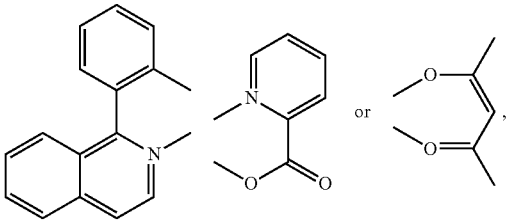

wherein Ph is phenyl.

14. The complex of Item 3, wherein the complex is represented by the following formulas IIIa, IIIb and their stereo isomers:

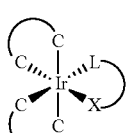

IIIa

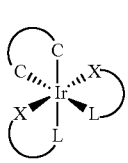

IIIb wherein the non-conjugated cyclometalated ligands are represented by C and C linked with an arch, and has a formula of $Ar_8$—$C(R_1R_2)$—$Ar_9$, wherein $Ar_8$ is aromatic ring, $Ar_9$ is N-heterocyclic carbene, $R_1$ and $R_2$ independently are H or methyl, wherein C in the formulas IIIa and IIIb is a carbon atom contained in $Ar_8$ and $Ar_9$; the ligated chromophore is presented by the L and X linked with an arch, and has formula of $Ar_3$—$Ar_4$, wherein $Ar_3$ and $Ar_4$ independently are an aromatic ring or N-heterocyclic ring, or $Ar_3$—$Ar_4$ together are

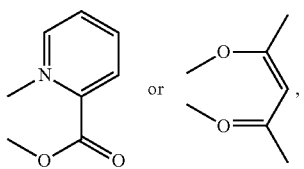

wherein L is N or O, and X is C, N or O.

15. The complex of Item 14, wherein the non-conjugated cyclometalated ligands are

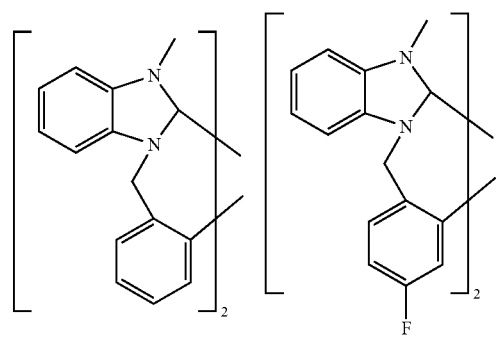

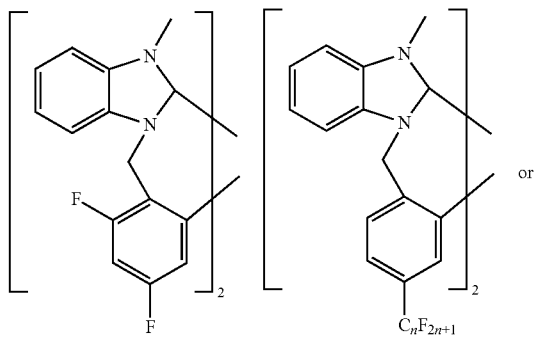

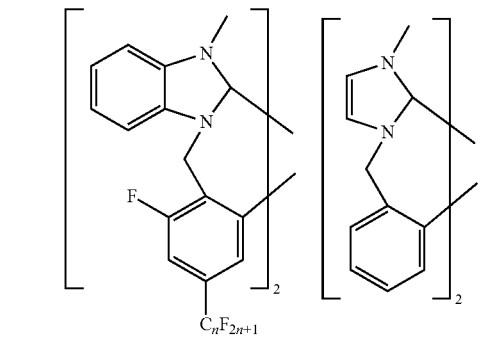

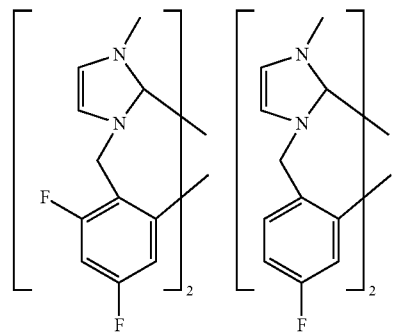

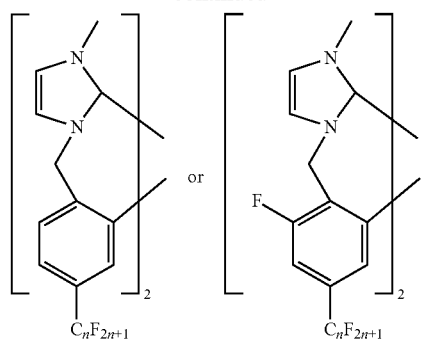

wherein n is an integer of 1-3.

16. The complex of Item 15, wherein positions of F and $C_nF_{2n+1}$ groups on phenyl rings of the two identical non-conjugated cyclometalated ligands are varied, and n is 1.

17. The complex of Item 16, wherein F and $C_nF_{2n+1}$ groups on phenyl rings of the non-conjugated cyclometalated ligands are independently replaced by CN group.

18. The complex of Item 14, wherein the ligated chromophores are

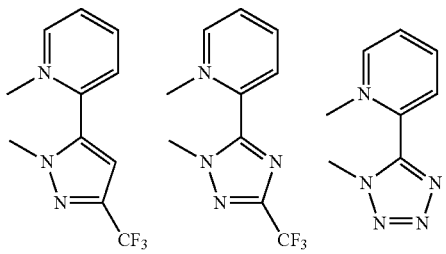

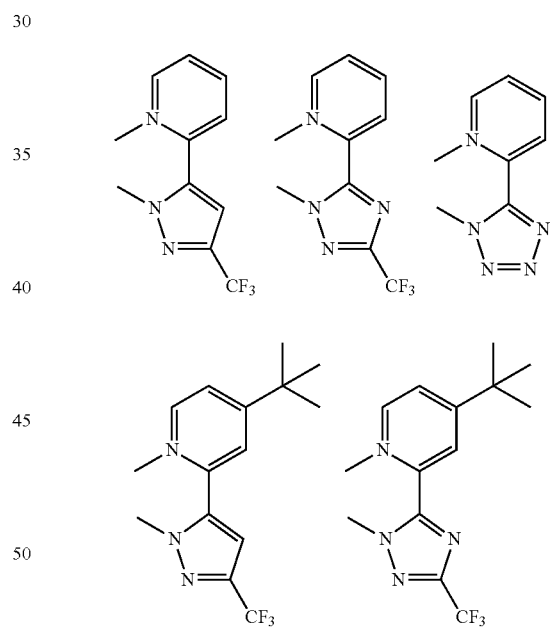

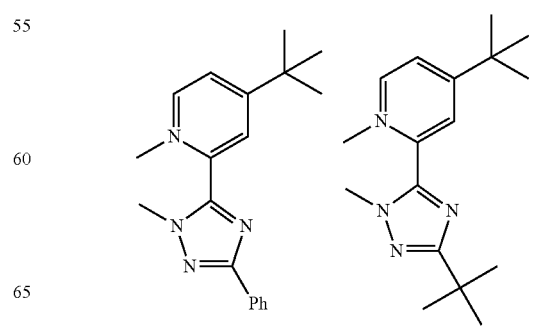

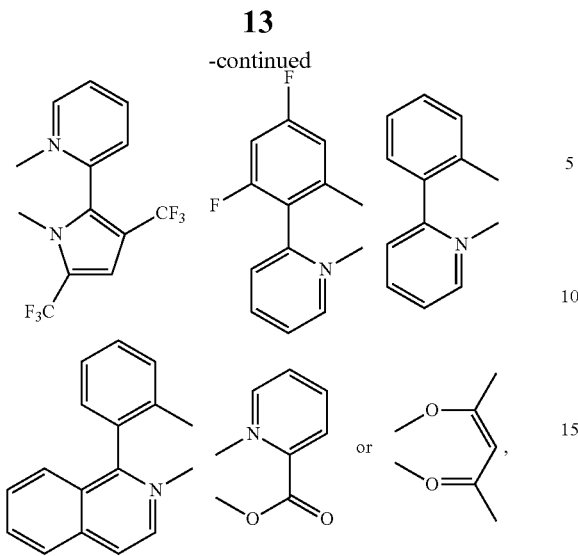

wherein Ph is phenyl.

The present invention also provides a phosphorescent organic light emitting diode comprising the phosphorescent tris-chelated metal complex as defined in any one of Items 1 to 15 as an emitting or emitter dopant material.

In one of the preferred embodiments of the present invention, the cyclometalated N-heterocyclic donors with an aliphatic spacer located at the ligand center would serve as some much better candidates in constructing such molecular design. The non-conjugated nature of these spacer will interrupt the π-conjugation of the chelating ligands, which then lowers the relative energy of the ligand-centered π-orbitals and destabilizing the respective π*-orbitals. With the assistance of this basic designing principle and the incorporation of the third chelating chromophores with a rigid and slightly lower-energy π-framework, metal complexes with efficient phosphorescent emission ranging from red, green and even true-blue can be successfully prepared.

The present invention will be better understood through the following examples, where are for illustrative only and not for limiting the scope of the present invention.

Preparation Examples 1-4

Synthesis of Non-Conjugated C^N Ligand

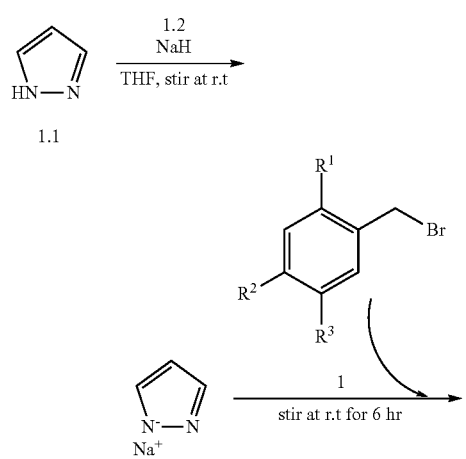

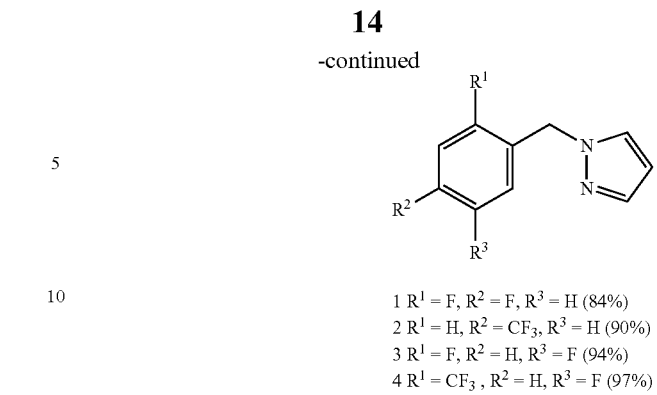

1 $R^1 = F, R^2 = F, R^3 = H$ (84%)
2 $R^1 = H, R^2 = CF_3, R^3 = H$ (90%)
3 $R^1 = F, R^2 = H, R^3 = F$ (94%)
4 $R^1 = CF_3, R^2 = H, R^3 = F$ (97%)

Preparation Example 1

2,4-difluorobenzyl-N-pyrazole (1)

To a suspension of NaH (1.31 g, 54.8 mmol) in THF (25 mL) at 0° C. was added pyrazole (3.42 g, 50.2 mmol) under $N_2$. The mixture was stirred until the evolution of hydrogen had finished. A solution of 2,4-difluorobenzylbromide (6.0 mL, 45.7 mmol) in dry THF (10 mL) was added dropwise. The reaction mixture was stirred at room temperature for 12 h. Resulting salt was then removed by filtration. Pure product was obtained after column chromatography using ethyl acetate as eluent, giving 7.26 g of light yellow liquid (38.8 mmol, 84%).

Spectral data of 1. $^1$H NMR (400 MHz, $CDCl_3$, 294 K): δ 7.52 (d, J=2.0 Hz, 1H, CH), 7.42 (d, J=2.0 Hz, 1H, CH), 7.15~7.10 (m, 1H, CH), 6.85~6.79 (m, 2H, CH), 6.26 (t, J=2.0 Hz, 1H, CH), 5.30 (s, 2H, $CH_2$).

Preparation Example 2

3-trifluoromethylbenzyl-N-pyrazole (2)

Ligand 2 was obtained in 90% by the similar procedure described for ligand 1 in Preparation Example 1.

Spectral data of 2. NMR (300 MHz, $CDCl_3$, 294 K): δ 7.58~7.55 (m, 4H, CH), 7.41 (d, J=2.2 Hz, 1H, CH), 7.25 (d, J=8.6 Hz, 1H, CH), 6.30 (t, J=2.2 Hz, 1H, CH), 5.37 (s, 2H, $CH_2$).

Preparation Example 3

2,5-difluorobenzyl-N-pyrazole (3)

Ligand 3 was obtained in 94% by the similar procedure described for ligand 1 in Preparation Example 1.

Spectral data of 3. $^1$H NMR (300 MHz, $CDCl_3$, 294 K): δ 7.54 (d, J=13 Hz, 1H, CH), 7.45 (d, J=1.7 Hz, 1H, CH), 7.05~6.91 (m, 2H, CH), 6.76~6.70 (m, 1H, CH), 6.29 (t, J=1.7 Hz, 1H, CH), 5.34 (s, 2H, $CH_2$).

Preparation Example 4

2-trifluoromethyl-5-fluorobenzyl-N-pyrazole (4)

Ligand 4 was obtained in 90% by the similar procedure described or ligand 1 in Preparation Example 1.

Spectral data of 4. $^1$H NMR (300 MHz, CDCl$_3$, 294 K): δ 7.67 (m, 2H, CH), 7.44 (d, J=2.0 Hz, 1H, CH), 7.03 (t, J=7.8 Hz, 1H, CH), 6.50 (d, J=9.5 Hz, 1H, CH), 6.35 (t, J=2.0 Hz, 1H, CH), 5.53 (s, 2H, CH$_2$).
Examples 1a-4b
Synthesis of Ir(C^N)$_2$LX
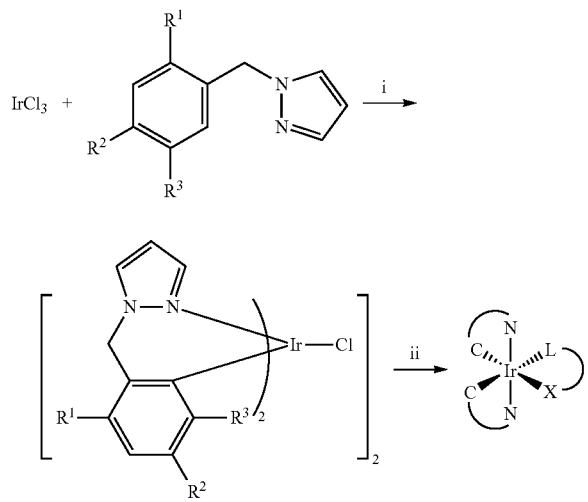
i. Reflux in 2-methoxyetnanol for 24 hr
ii. Addition of third ligand and Na$_2$CO$_3$, stir at RT more 12 hr
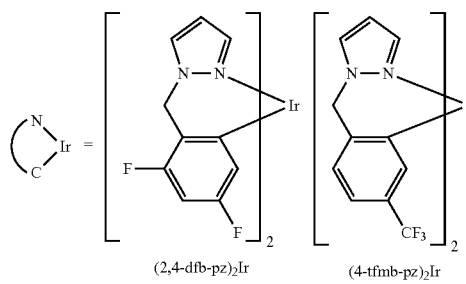
(2,4-dfb-pz)$_2$Ir    (4-tfmb-pz)$_2$Ir
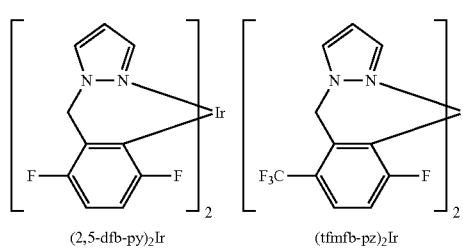
(2,5-dfb-py)$_2$Ir    (tfmfb-pz)$_2$Ir
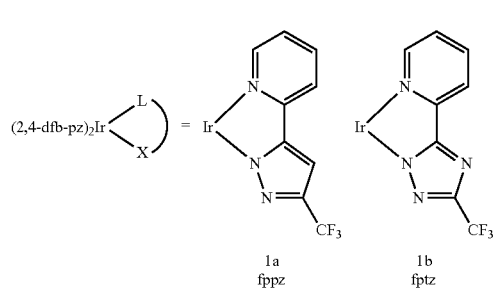
1a fppz    1b fptz
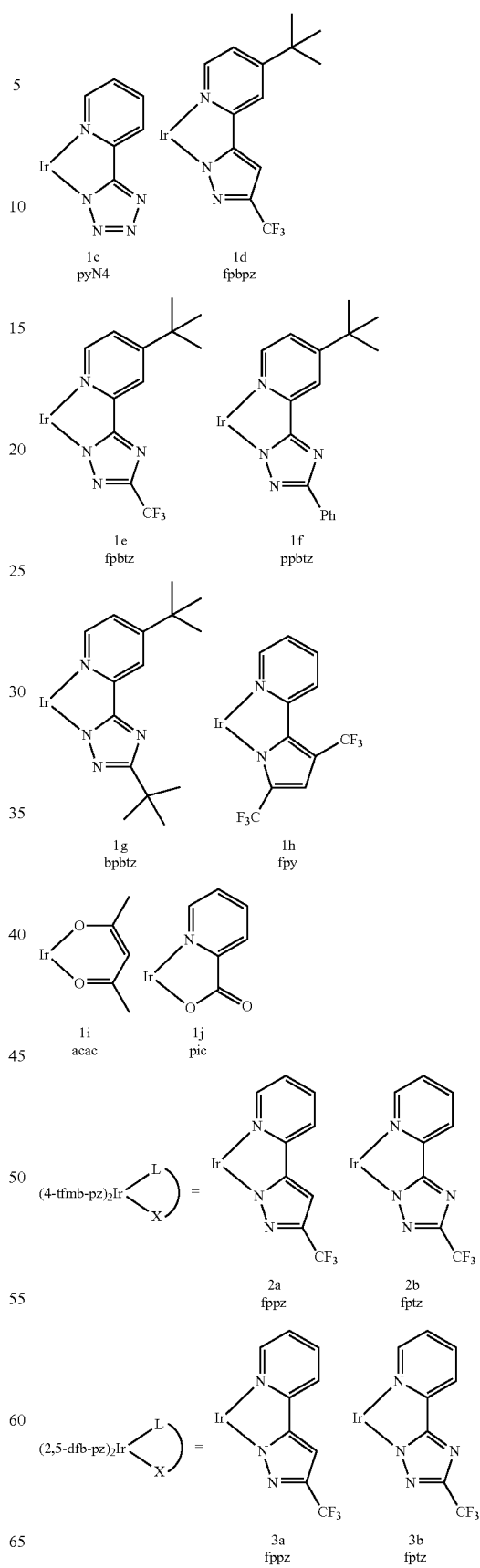
1c pyN4    1d fpbpz
1e fpbtz    1f ppbtz
1g bpbtz    1h fpy
1i acac    1j pic
2a fppz    2b fptz
3a fppz    3b fptz

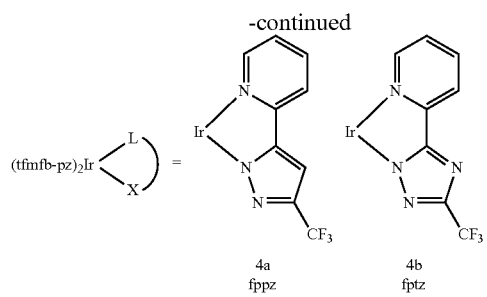

4a fppz    4b fptz

Ir(2,4-dfb-pz)$_2$LX Series (1a-1j)

Synthetic method of preparing this series of iridium complexes [Ir(2,4-dfb-pz)$_2$(L^X)] were much better executed by heating of a 2:1 mixture of (2,4-d-pz)H and IrCl$_3$.3H$_2$O in methoxyethanol (140° C., 24 hr), followed by treatment with 1.1 equiv. of chelating anions (L^X)H in presence of proton scavenger Na$_2$CO$_3$ (RT, 8 hr), for which several representative examples for the L^X ligands are shown in Chart of Fig. 4. The isolated products are separated by column chromatography on silica gel eluting with a mixture of ethyl acetate and hexane (1:1). It is believed that the reaction proceeded via the formation of an intermediate with proposed formula [Ir(2,4-dfb-pz)$_2$(μ-Cl)]$_2$. After then, addition of the chelating anion (L^X) would induce the rapid cleavage of dimer, giving the monometallic products with formula [Ir(2,4-dfb-pz)$_2$(L^X)]. Moreover, if the reactions with L^X ligand were conducted in refluxing methoxyethanol, a reduction of product yield was noted, which showed the intricate nature of such substitution reaction.

Example 1a

Ir(2,4-dfb-pz)$_2$(fppz) (1a)

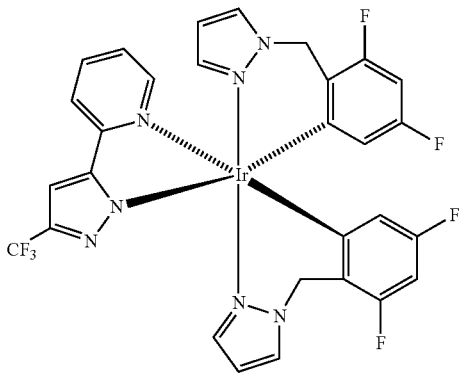

A mixture of 2,4-difluorobenzyl-N-pyrazole (0.23 g, 1.18 mmol) and IrCl$_3$.3H$_2$O (0.20 g, 0.57 mmol) in 2-methoxyethanol (5 mL) was reflux for 24 hours under nitrogen. After cooling the solution to room temperature, 3-trifluoromethyl-5-(2-pyridyl) pyrazole (0.12 g, 0.567 mmol) and Na$_2$CO$_3$ (60 mg, 0.567 mmol) was added and the mixture was stir at RT for further 12 hours. Excess of water was added and the resulting precipitate was collected by filtration and washed with MeOH. Further purification was conducted by silica gel column chromatography using CH$_2$Cl$_2$ as eluent, giving 0.22 g of pearl solid (0.278 mmol, 49%).

Spectral data of 1a: MS (FAB), m/z 792, (M+1)$^+$. $^1$H NMR (500 MHz, d-acetone, 194 K): δ 8.80 (d, J=5.5 Hz, 1H, CH), 8.32 (d, J=2.0 Hz, 1H, CH), 8.24 (d, J=2.0 Hz, 1H, CH), 8.08 (d, J=3.5 Hz, 2H, CH), 7.50 (m, 1H, CH), 7.37 (d, J=2.0 Hz, 1H, CH), 7.26 (s, 1H, CH), 7.00 (d, J=2.0 Hz, 1H, CH), 6.69 (td, J=10.0 Hz, 2.0 Hz, 1H, CH), 6.56 (td, J=10.0 Hz, 2.0 Hz, 1H, CH), 6.43 (t, J=2.0 Hz, 1H, cm, 6.36 (t, J=2.0 Hz, 1H, CH), 6.02 (d, J=14.5 Hz, 1H, CH$_2$), 5.97 (d, J=16.0 Hz, 1H, CH$_2$), 5.86 (d, J=14.5 Hz, 1H, CH$_2$), 5.05 (dd, J=10.0 Hz, 2.0 Hz, 1H, CH), 5.00 (d, J=16.0 Hz, 1H, CH$_2$), 4.72 (dd, J=10.0 Hz, 2.0 Hz, 1H, CH). $^{19}$F NMR (470 MHz, d-acetone, 194 K): δ −59.70 (s, 3F, CF$_3$), −115.09 (s, 1F, CF), −115.77 (s, 1F, CF), −117.73 (s, 1F, CF), −119.71 (s, 1F, CF). Anal. Calcd. For C$_{29}$H$_{19}$F$_7$IrN$_7$: N, 12.40; C, 44.05; H, 2.42. Found: N, 11.63; C, 43.64; H, 2.69.

Example 1b

Ir(2,4-dfb-pz)$_2$(fptz) (1b)

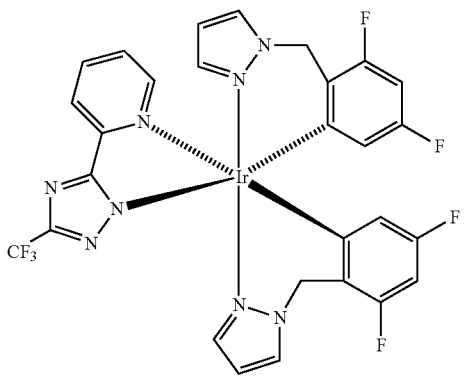

A mixture of 2,4-difluorobenzyl-N-trazole (0.35 g, 1.79 mmol) and IrCl$_3$.3H$_2$O (0.30 g, 0.851 mmol) in 2-methoxyethanol (5 mL) was reflux for 24 hours under nitrogen. After cooling the solution to room temperature, 3-trifluoromethyl-5-(2-pyridyl)triazole (182 mg, 0.851 mmol) and Na$_2$CO$_3$ (90 mg, 0.851 mmol) was added and the mixture was stir at RT for further 12 hours. Excess of water was added and the resulting precipitate was collected by filtration and washed with MeOH and ether. Further purification was conducted by recrystallization using acetone/hexane, giving 0.40 g of colorless solid (0.501 mmol, 59%).

Spectral data of 1b: MS (FAB), m/z 793, (M+1)$^+$. $^1$H NMR (400 MHz, d-acetone, 294 K): δ 8.78 (br, 1H, CH), 8.19~8.15 (m, 3H, CH), 8.11 (d, J=2.8 Hz, 1H, CH), 8.65 (m, 1H, CH), 7.19 (s, 1H, CH), 6.98 (s, 1H, CH), 6.57 (td, J=9.6 Hz, 2.4 Hz, 1H, CH), 6.45 (td, J=9.6 Hz, 2.4 Hz, 1H, CH), 6.32 (t, 2.4 Hz, 1H, CH), 6.30 (t, J=2.4 Hz, 1H, CH), 5.79 (d, J=14.8 Hz, 1H, CH$_2$), 5.61 (br, 2H, CH+CH$_2$), 5.36 (br, 2H, CH+CH$_2$), 5.14

(d, J=15.2 Hz, 1H, CH$_2$). Anal. Calcd. For C$_{28}$H$_{18}$F$_7$IrN$_8$: N, 14.15; C, 42.48; H, 2.29. Found: N, 13.53; C, 42.28; H, 2.62.

Example 1c

Ir(2,4-dfb-pz)$_2$(pyN4) (1c)

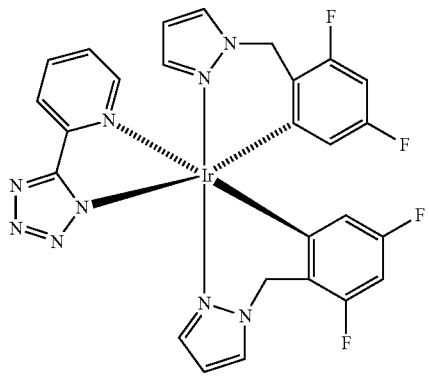

Compound 1c was obtained in 42% by the similar procedure described for the complex 1b in Example 1b.

Spectral data of 1c: MS (FAB), m/z 726, (M+1)$^+$. $^1$H NMR (300 MHz, d-acetone, 294 K): δ 8.81 (br, 1H, CH), 8.34 (d, J=7.9 Hz, 1H, CH), 8.23 (td, J=7.9 Hz, 1.5 Hz, 1H, CH), 8.18 (d, J=2.4 Hz, 1H, CH), 8.12 (d, J=2.4 Hz, 1H, CH), 7.69 (ddd, J=7.9 Hz, 5.7 Hz, 1.2 Hz, 1H, CH), 7.17 (s, 1H, CH), 6.85 (s, 1H, CH), 6.60 (ddd, J=2.4 Hz, 1H, CH), 6.50 (ddd, J=14.8 Hz, 1H, CH$_2$), 6.33 (t, J=2.5 Hz, 1H, CH), 6.29 (t, J=2.5 Hz, 1H, CH), 5.70 (m, 3H, CH+CH$_2$), 5.40 (br, 1H, CH), 5.16 (d, J=15.5 Hz, 2H, CH$_2$).

Example 1d

Ir(2,4-dfb-pz)$_2$(fpbpz) (1d)

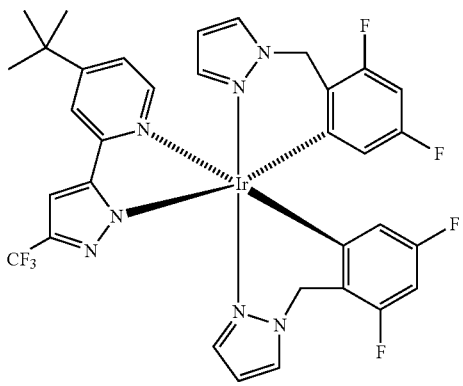

Compound 1d was obtained in 32% by the similar procedure described for the compound 1a in Example 1a. Purification was conducted by silica gel column chromatography using EA/hexane (1:2) as eluent.

Spectral data of 1d: MS (FAB), m/z 848, (M+1)$^+$. $^1$H NMR (400 MHz, d-acetone, 294 K): δ 8.55 (d, J=5.0 Hz, 1H, CH), 8.13 (d, J=2.4 Hz, 1H, CH), 8.08~8.05 (m, 2H, CH), 7.46 (dd, J=6.0 Hz, 2.4 Hz, 1H, CH), 7.19 (s, 1H, CH), 7.16 (s, 1H, CH), 7.03 (s, 1H, CH), 6.53 (td, J=9.6 Hz, 2.4 Hz, 1H, CH), 6.39 (td, J=9.6 Hz, 2.4 Hz, 1H, CH), 6.31 (t, J=2.4 Hz, 1H, CH), 6.27 (t, J=2.4 Hz, 1H, CH), 6.00 (d, J=14.8 Hz, 1H, CH$_2$), 5.67 (br, 3H, CH+CH$_2$), 5.34 (br, 1H, CH), 5.08 (d, J=15.6 Hz, 1H, CH$_2$), 1.37 (s, 9H, CH$_3$). Anal. Calcd. For C$_{33}$H$_{27}$F$_7$IrN$_7$: N, 11.58; C, 46.80; H, 3.21. Found: N, 10.44; C, 47.72; H, 3.73.

Example 1e

Ir(2,4-dfb-pz)$_2$(fpbtz) (1e)

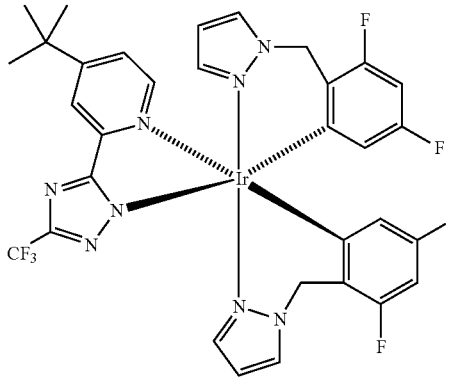

Compound 1e was obtained in 40% by the similar procedure described for the compound 1a in Example 1a. Purification was conducted by silica gel column chromatography using EA/hexane (2:3) as eluent.

Spectral data of 1e: MS (FAB), Ink 849, (M+1)$^+$. $^1$H NMR (400 MHz, d-acetone, 294 K): δ 8.65 (br, 1H, CH), 8.16~8.10 (m, 3H, CH), 7.68 (dd, J=5.6 Hz, 1.6 Hz, 1H, CH), 7.16 (s, 1H, CH), 6.97 (s, 1H, CH), 6.57 (ddd, J=10.2 Hz, 8.6 Hz, 2.4 Hz, 1H, CH), 6.44 (ddd, J=10.2 Hz, 8.6 Hz, 2.4 Hz, 1H, CH), 6.32 (t, J=2.4 Hz, 1H, CH), 6.29 (t, J=2.4 Hz, 1H, CH), 5.79 (d, J=14.0 Hz, 1H, CH$_2$), 5.62 (br, 3H, CH+CH$_2$), 5.37 (br, 1H, CH), 5.12 (d, J=15.6 Hz, 1H, CH$_2$), 1.41 (s, 9H, CH$_3$). Anal. Calcd. For C$_{32}$H$_{26}$F$_7$IrN$_8$: N, 13.22; C, 45.33; H, 3.09. Found: N, 12.90; C, 45.37; H, 3.41.

Example 1f

Ir(2,4-dfb-pz)$_2$(ppbtz) (1f)

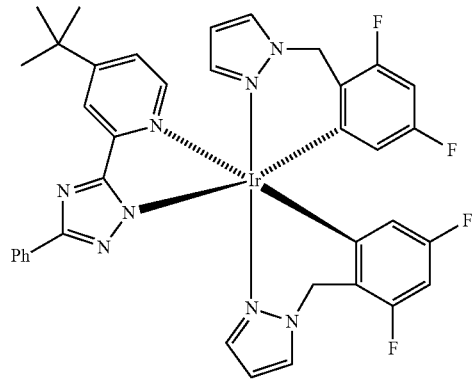

Compound 1f was obtained in 40% by the similar procedure described for the parent compound 1a in Example 1a.

Purification was conducted by silica gel column chromatography using $CH_2Cl_2$ as eluent.

Spectral data of 1f: MS (FAB), m/z 857, (M+H)$^+$. $^1$H NMR (400 MHz, d-acetone, 294 K): δ 8.62 (d, J=5.4 Hz, 1H, CH), 8.18~8.15 (m, 3H, CH), 8.13 (d, J=2.4 Hz, 1H, CH), 8.08 (d, J=-2.4 Hz, 1H, CH), 7.58 (dd, J=6.0 Hz, 2.4 Hz, 1H, CH), 7.40~7.27 (m, 2H, CH), 7.29 (td, J=7.6 Hz, 2.0 Hz, 1H, CH), 7.19~7.16 (m, 2H, CH), 6.55 (ddd, J=10.4 Hz, 9.2 Hz, 2.4 Hz, 1H, CH), 6.44 (ddd, J=10.4 Hz, 9.2 Hz, 2.4 Hz, 1H, CH), 6.30 (t, J=2.4 Hz, 1H, CH), 6.25 (t, J=2.4 Hz, 1H, CH), 6.12~5.61 (br, 2H, CH+CH$_2$), 5.38~5.07 (br, 4H, CH), 1.40 (s, 9H, CH$_3$). Anal. Calcd. for $C_{37}H_{31}F_4IrN_8 \cdot CH_2Cl_2$: N, 11.91; C, 48.51; H, 3.54. Found: N, 12.08; C, 48.60; H, 3.75.

Example 1g

Ir(2,4-dfb-pz)$_2$(bpbtz) (1g)

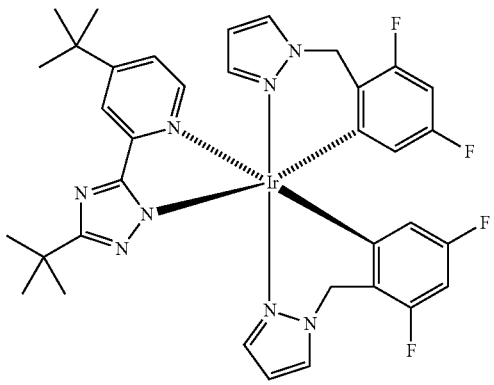

Compound 1g was obtained in 63% by the similar procedure described for the parent compound 1a in Example 1a. Purification was conducted by flash column chromatography using $CH_2Cl_2$ as eluent.

Spectral data of 1g: MS (FAB), m/z 837, (M+1)$^+$. $^1$H NMR (400 MHz, d-acetone, 294 K): δ 8.60 (d, J=6.0 Hz, 1H, CH), 8.11 (d, J=2.4 Hz, 1H, CH), 8.06 (d, J=2.4 Hz, 1H, CH), 7.99 (s, 1H, CH), 7.52 (dd, J=6.0 Hz, 2.4 Hz, 1H, CH), 7.18 (s, 1H, CH), 7.12 (br, 1H, CH), 6.52 (ddd, J=10.8 Hz, 8.8 Hz, 2.4 Hz, 1H, CH), 6.39 (ddd, J=10.4 Hz, 9.2 Hz, 2.4 Hz, 1H, CH), 6.30 (t, J=2.4 Hz, 1H, CH), 6.25 (t, J=2.4 Hz, 1H, CH), 6.12 (d, J=15.6 Hz, 1H, CH$_2$), 5.84~5.26 (br, 3H, CH+CH$_2$), 5.01~4.88 (m, 2H, CH+CH$_2$), 1.37 (s, 9H, CH$_3$), 1.35 (s, 9H, CH$_3$). Anal. calcd. for $C_{35}H_{35}F_4IrN_8 \cdot 0.5CH_2Cl_2$: N, 12.76; C, 48.54; H, 4.13. Found: N, 12.55; C, 48.16; H, 4.25.

Example 1h

Ir(2,4-dfb-pz)$_2$(fpy) (1h)

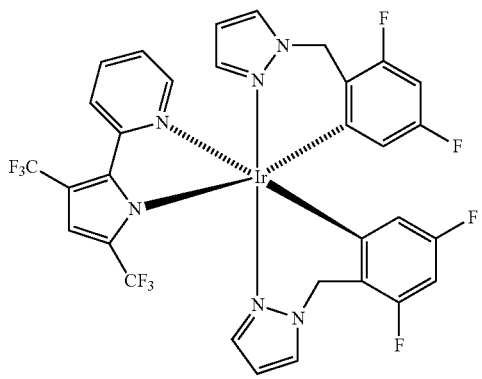

Compound 1h was obtained in 24% by the similar procedure described for the parent compound 1a in Example 1a. Purification was conducted by column chromatography using $CH_2Cl_2$/hexane (1:2) as eluent.

Spectral data of BE MS (FAB), m/z 858, (M)$^+$. $^1$H NMR (400 MHz, d-acetone, 294 K): δ 8.25 (d, J=8.0 Hz, 1H, CH), 8.12 (dd, J=9.2 Hz, 2.4 Hz, 2H, CH), 8.01 (ddd, J=8.8 Hz, 8.0 Hz, 1.2 Hz, 1H, CH), 7.85 (d, J=5.6 Hz, 1H, CH), 7.13~7.10 (m, 2H, CH), 6.87 (s, 1H, CH), 6.71 (d, J=2.4 Hz, 1H, CH), 6.63 (ddd, J=12.8 Hz, 9.2 Hz, 2.8 Hz, 1H, CH), 6.47~6.40 (m, 2H, CH), 6.37 (t, J=2.4 Hz, 1H, CH), 6.34 (t, J=2.4 Hz, 1H, CH), 6.28 (d, J=10.0 Hz, 1H, CH), 5.56 (d, J=15.2 Hz, 1H, CH$_2$), 5.52 (d, J=15.2 Hz, 1H, CH$_2$), 4.72 (d, J=15.2 Hz, 1H, CH$_2$), 4.69 (d, J=15.2 Hz, 1H, CH$_2$). Anal. Calcd. For $C_{31}H_{19}F_{10}IrN_6$: N, 9.80; C, 43.41; H, 2.23. Found: N, 9.81; C, 43.44; H, 2.58.

Example 1i

Ir(2,4-dfb-pz)$_2$(acac) (1i)

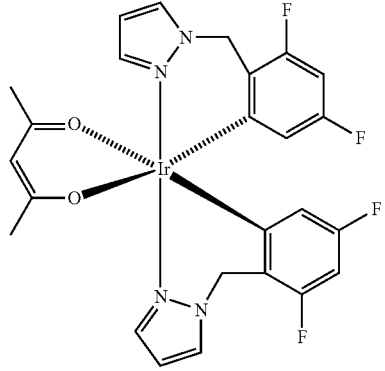

Compound 1i was obtained in 72% by the similar procedure described for the parent compound 1a in Example 1a. Purification was conducted by column chromatography using EA/hexane (1:1) as eluent and recrystallization using $CH_2Cl_2$ and hexane.

Spectral data of 1i: MS (FAB), m/z 678, (M)$^+$. $^1$H NMR (400 MHz, d-acetone, 294 K): δ 8.14 (d, J=2.0 Hz, 2H, CH), 7.41 (br, 2H, CH), 6.49 (t, J=2.0 Hz, 2H, CH), 6.34 (td, J=8.0 Hz, 1.6 Hz, 2H, CH), 5.59~5.12 (m, 7H, CH+CH$_2$), 1.84 (s, 6H, CH$_3$). Anal. Calcd. For $C_{25}H_{21}F_4IrN_4O_2 \cdot CF_{12}Cl_2$: N, 7.35; C, 40.95; H, 3.04. Found: N, 7.47; C, 41.14; H, 3.37.

Example 1j

Ir(2,4-dfb-pz)$_2$(pic) (1j)

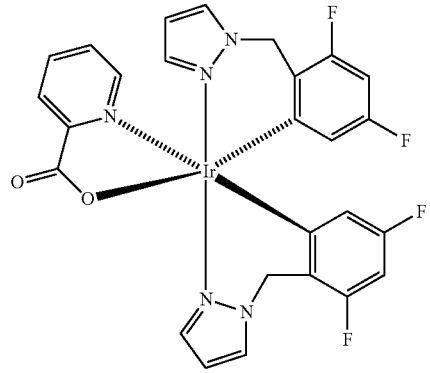

Compound 1j was obtained in 30% by the similar procedure described for the parent compound 1a in Example 1a.

Purification was conducted by column chromatography using EA/hexane (2:1) as eluent and recrystallization using $CH_2Cl_2$ and MeOH.

Spectral data of 1j: MS (FAB), m/z 702, (M+1)$^+$. $^1$H NMR (400 MHz, CDCl$_3$, 294 K): δ 8.35 (br, 2H, CH), 7.96 (t, J=8.0 Hz, 1H, CH), 7.62 (d, J=2.4 Hz, 1H, CH), 7.57 (d, J=2.4 Hz, 1H, CH), 7.50 (t, J=6.4 Hz, 1H, CH), 7.40 (d, J=2.4 Hz, 1H, CH), 6.86 (d, J=2.4 Hz, 1H, CH), 6.43 (td, J=9.6 Hz, 2.4 Hz, 1H, CH), 6.31 (td, J=9.6 Hz, 2.4 Hz, 1H, CH), 6.27 (t, J=2.4 Hz, 1H, CH), 6.19 (t, J=2.4 Hz, 1H, CH), 5.62~4.97 (br, 6H, CH+CH$_2$). Anal. Calcd. For $C_{26}H_{18}F_4IrN_5O_2$: N, 10.00; C, 44.57; H, 2.59. Found: N, 9.82; C, 45.15; H, 2.96.

4.1 Ir(4-CF$_3$b-pz)$_2$LX Series (2a-2b)

Example 2a

Ir(4-tfmb-pz)$_2$(fppz) (2a)

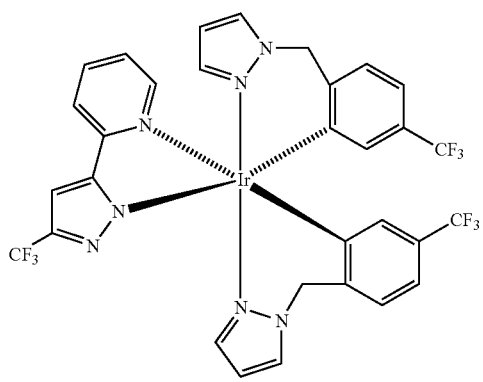

A mixture of 4-trifluoromethylbenzyl-N-pyrazole (0.20 g, 0.89 mmol) and IrCl$_3$·3H$_2$O (0.15 g, 0.43 mmol) in 2-methoxyethanol (5 mL) was reflux for 24 hours under nitrogen. After cooling the solution to room temperature, 3-trifluoromethyl-5-(2-pyridyl)pyrazole (91 mg, 0.43 mmol) and Na$_2$CO$_3$ (0.23 g, 2.17 mmol) was added and the mixture was stir at RT for further 12 hours. Excess of water was added and the resulting precipitate was collected by filtration. Further purification was conducted by flash column chromatography using $CH_2Cl_2$ as eluent, giving 127 mg of yellow powder (0.149 mmol, 35%).

Spectral data of 2a: MS (FAB), m/z 856, (M+1)$^+$. $^1$H NMR (400 MHz, d-acetone, 294 K): δ 8.57 (br, 1H, CH), 8.04~7.98 (m, 3H, CH), 7.96 (d, J=2.4 Hz, 1H, CH), 7.40 (td, J=5.6 Hz, 2.4 Hz, 1H, CH), 7.29 (d, J=8.0 Hz, 1H, CH), 7.18~7.15 (m, 3H, CH), 7.11 (s, 1H, CH), 7.03~6.98 (m, 2H, CH), 6.28 (t, J=2.4 Hz, 1H, CH), 6.23 (t, J=2.4 Hz, 1H, CH), 6.08~5.81 (br, 3H, CH+CH$_2$), 5.48~5.29 (m, 3H, CH+CH$_2$). Anal. Calcd. For $C_{31}H_{21}F_9IrN_7$: N, 11.47; C, 43.56; H, 2.48. Found: N, 11.02; C, 44.15; H, 2.99.

Example 2b

Ir(4-tfmb-pz)$_2$(fptz) (2b)

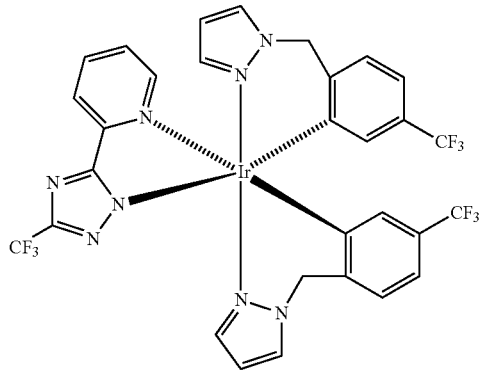

Compound 2b was obtained in 31% by the similar procedure described for the parent compound 2a in Example 2a. Purification was conducted by flash column chromatography using $CH_2Cl_2$ as eluent.

Spectral data of 2b: MS (FAB), m/z 857, (M+1)$^+$. $^1$H NMR (400 MHz, d-acetone, 294 K): δ 8.70 (br, 1H, CH), 8.20~8.14 (m, 2H, CH), 8.06 (d, J=2.4 Hz, 1H, CH), 7.99 (d, J=2.4 Hz, 1H, CH), 7.63 (td, J=6.4 Hz, 2.4 Hz, 1H, CH), 7.33 (d, J=8.0 Hz, 1H, CH), 7.23~7.18 (m, 3H, CH), 7.06 (d, J=6.4 Hz, 1H, CH), 6.99 (d, J=2.4 Hz, 1H, CH), 6.30 (t, J=2.4 Hz, 1H, CH), 6.26 (d, J=2.4 Hz, 1H, CH$_2$), 6.06~5.75 (br, 3H, CH+CH$_2$), 5.53~5.37 (m, 3H, CH+CH$_2$). Anal. Calcd. For $C_{30}H_{20}F_9IrN_8$: N, 13.09; C, 42.11; H, 2.36. Found: N, 12.84; C, 42.10; H, 2.66.

Ir(2,5-dfb-pz)$_2$LX Series (3a-3b)

Example 3a

Ir(2,5-dfb-pz)$_2$(fppz) (3a)

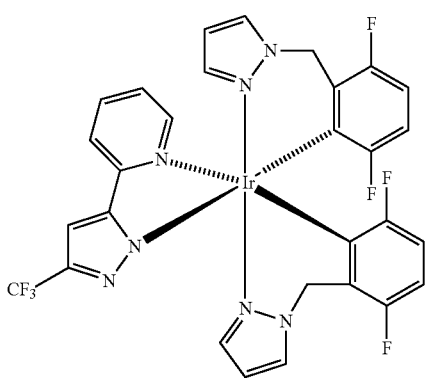

Compound 3a was obtained in 28% by the similar procedure described for the parent compound 1a in Example 1a. Purification was conducted by column chromatography using $CH_2Cl_2$ as eluent.

Spectral data of 3a: MS (FAB), m/z 792, (M+1)+ Anal. Calcd. For $C_{29}H_{19}F_7IrN_7 \cdot CH_3COCH_3$: N, 11.55; C, 45.28; H, 2.97. Found: N, 11.11; C, 45.51; 3.28.

Example 3b

Ir(2,5-dfb-pz)$_2$(fptz) (3b)

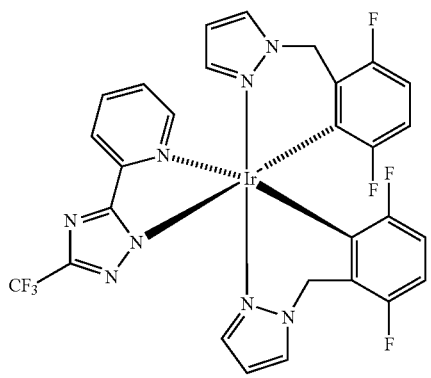

Compound 3b was obtained in 30% by the similar procedure described for the parent compound 1a in Example 1a. Purification was conducted by column chromatography using $CH_2Cl_2$ as eluent and recrystallization using $CH_2Cl_2$ and hexane.

Spectral data of 3b: MS (FAB), m/z 793, (M+1)+. $^{19}$F NMR (470 MHz, d-acetone, 294 K): δ −63.31 (s, 3F, CF$_3$, 3b'), −63.42 (s, 3F, CF$_3$, 3b), −104.73 (s, 1F, CF, 3b'), 105.85 (s, 1F, CF, 3b), −106.72 (s, 1F, CF, 3b'), −109.91 (s, 1F, CF, 3b), −124.88 (s, 1F, CF, 3b'), −125.53 (s, 1F, CF, 3b), −126.10 (s, 1F, CF, 3b'), −126.64 (s, 1F, CF, 3b). Anal. Calcd. For $C_{28}H_{18}F_7IrN_8$: N, 14.15; C, 42.48; H, 2.29. Found: N, 13.84; C, 42.26; H, 2.70.

Ir(tfmfb-pz)$_2$LX series (4a-4b)

Example 4a

Ir(tfmfb-pz)$_2$(fppz) (4a)

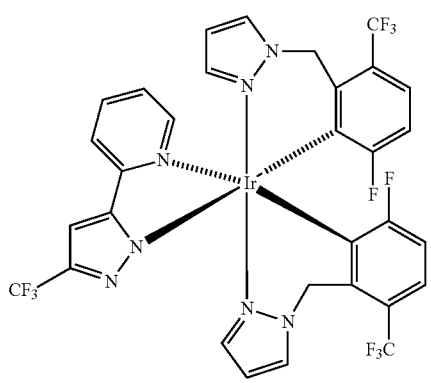

A mixture of 2-trifluoromethyl-5-fluorobenzyl-N-pyrazole (75 mg, 031 mmol) and $IrCl_3 \cdot 3H_2O$ (54 mg, 0.15 mmol) in 2-methoxyethanol (4 mL) was reflux for 2 days under nitrogen. After cooling the solution to room temperature, 3-trifluoromethyl-5-(2-pyridyl)pyrazole (33 mg, 0.15 mmol) and $Na_2CO_3$ (81 mg, 0.77 mmol) was added and the mixture was stir at RT for further 12 hours. Excess of water was added and the resulting precipitate was collected by filtration. Further purification was conducted by column chromatography using $CH_2Cl_2$/hexane (1:1) as eluent, giving 42 mg of white powder (0.05 mmol, 31%).

Spectral data of 4a: MS (FAB), m/z 892, (M+1)+. $^{19}$F NMR (470 MHz, d-acetone, 294 K): δ −57.14 (s, 6F, CF$_3$, 4a), −57.40 (s, 3F, CF$_3$, 4a'), −57.59 (s, 3F, CF$_3$, 4a'), −60.24 (s, 3F, CF$_3$, 4a'), −60.59 (s, 3F, CF$_3$, 4a), −88.20 (s, 1F, CF, 4a'), −91.21 (s, 1F, CF, 4a), −9154 (s, 1F, CF, 4a'), −95.02 (s, 1F, CF, 4a). Anal. Calcd. For $C_{31}H_{19}F_{11}IrN_7 \cdot CH_2Cl_2$: N, 10.05; C, 39.39; H, 2.17. Found: N, 10.02; C, 39.67; H, 2.55.

Example 4b

Ir(tfmtb-pz)$_2$(fptz) (4b)

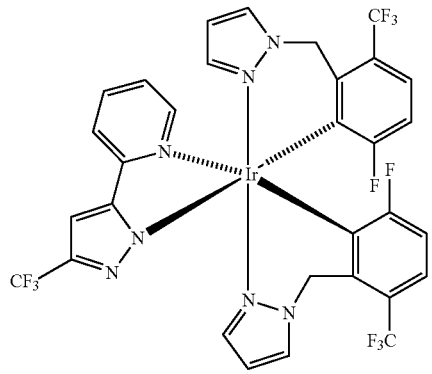

Compound 4b was obtained in 28% by the similar procedure described for the parent compound 4a in Example 4a. Purification was conducted by column chromatography using $CH_2Cl_2$/hexane (1:3) as eluent and recrystallization using $CH_2Cl_2$/hexane double layer system.

Spectral data of 4b: MS (FAB), m/z 893, (M+1)+. $^{19}$F NMR (470 MHz, d-acetone, 294 K): δ −57.21 (s, 6F, CF$_3$, 4b), −57.54 (s, 3F, CF$_3$, 4b'), −57.67 (s, 3F, CF$_3$, 4b'), −63.70 (s, 3F, CF$_3$, 4b'), −64.03 (s, 3F, CF$_3$, 4b), −88.72 (s, 1F, CF, 4b'), −91.34 (s, 1F, CF, 4b), 91.85 (s, 1F, CF, 4b'), −94.87 (s, 1F, CF, 4b). Anal. Calcd. For $C_{30}H_{18}F_{11}IrN_8 \cdot CH_2Cl_2$: N, 11.47; C, 38.12; H, 2.06. Found: N, 11.45; C, 38.31; H, 2.37.

Example 5a-5b

Synthesis of Ir(CAP)₂LX

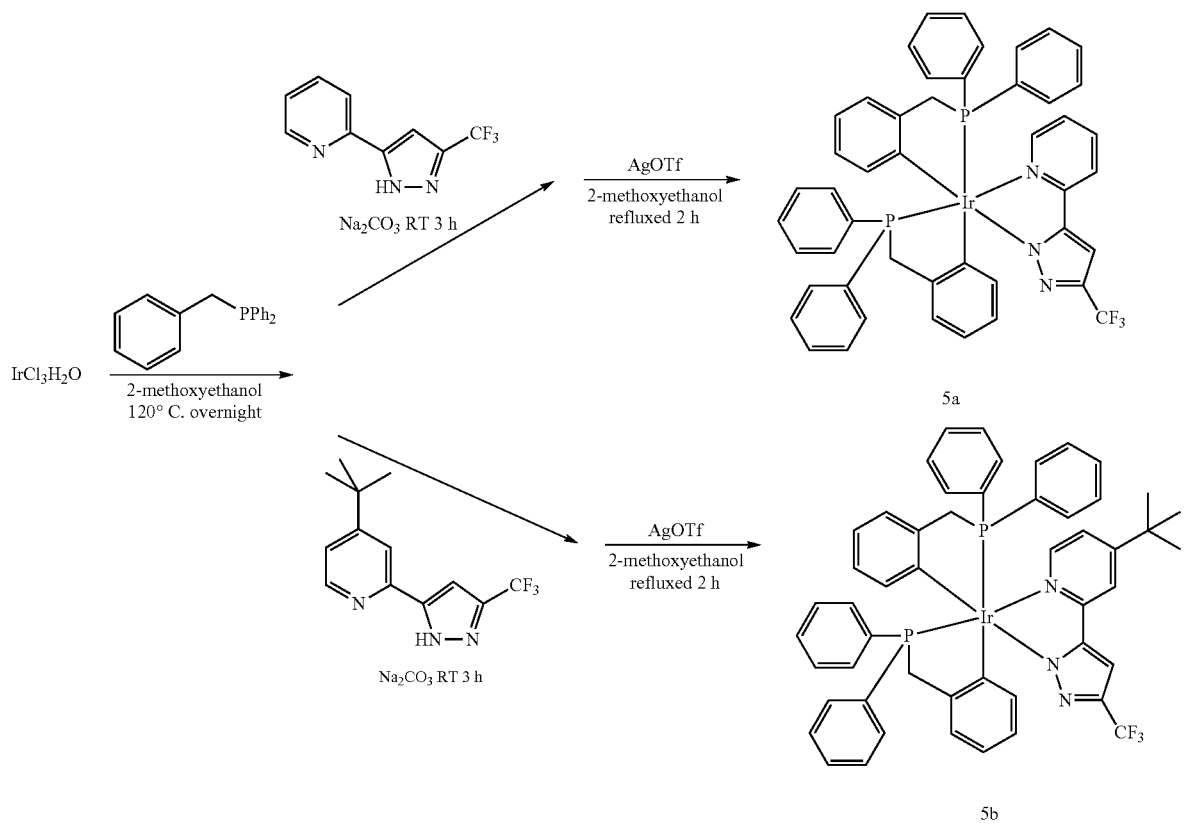

Example 5a

Ir(bdpp)₂(fppz) (5a)

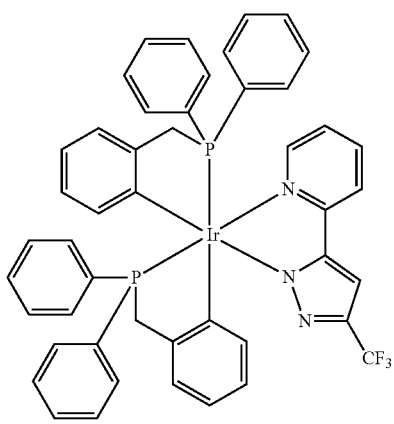

A 25 mL flask was charged with IrCl₃·3H₂O (210 mg, 0.6 mmol) and benzyldiphenyl phosphine (331 mg, 1.2 mmol) then dry and degassed 2-methoxyethanol (10 mL) was added as solvent. The reaction mixture was heated at 120° C. for 12 hour. After cooling to room temperature, fppzH (86 mg, 0.4 mmol) and Na₂CO₃ (636 mg, 6.0 mmol) were added into the flask, followed by stirring at RT for another 3 hour. The reaction was quenched by addition of excess water which resulted in the pale yellow precipitate. The precipitate was collected by the filtration and then washed with ice MeOH and diethyl ether. Purification by flash column using CH₂Cl₂ as eluent gave a chloride intermediate which could be further purified by recrystallization in mixed CH₂Cl₂ and hexane solution with 40% yield (240 mg, 0.24 mmol). After then, a mixture of chloride intermediate (99 mg, 0.1 mmol), AgOTf (28 mg, 0.12 mmol) and dry 2-methoxyethanol (5 mL) was refluxed in the dark for 2 hour and then cooled to room temperature. After removal of the white precipitate by filtration, the collected filtrate was added excess water. The resulting white precipitate could be collected by filtration, followed by washing with ice methanol and diethyl ether. Purification was conducted by flash column using CH₂Cl₂ as eluent and then recrystallization in mixed solution of CH₂Cl₂ and hexane gave 5a as white powder with 37% yield (70 mg, 0.037 mmol).

Spectral data of 5a: MS (FAB, $^{192}$Ir), 955 [M⁺]. ¹H NMR (500 MHz, CDCl₃, 294K): δ 7.89 (d, J=8.0 Hz, 1H), 7.87 (d, J=8.0 Hz, 1H), 7.50 (d, J=6.5 Hz, 1H), 7.43 (t, J=9.0 Hz, 2H), 7.33-7.25 (m, 3H), 7.21 (d, J=7.5 Hz, 1H), 7.16-7.13 (m, 3H), 7.11-7.08 (m, 5H), 6.96 (t, J=7.5 Hz, 1H), 6.85 (t, J=7.5 Hz, 1H), 6.82-6.79 (m, 3H), 6.77 (s, 1H), 6.72 (t, J=7.3 Hz, 1H), 6.69-6.66 (m, 3H), 6.61 (t, J=8.8 Hz, 2H), 6.43 (t, J=6.8 Hz, 1H), 6.32 (t, J=8.5 Hz, 2H), 6.18 (t, J=5.8 Hz, 1H), 4.05 (dd, J=15.0, 8.8 Hz, 1H), 3.77 (dd, J=15.0, 8.8 Hz, 1H), 3.46 (dd, J=16.5, 9.7 Hz, 1H), 2.17 (dd, J=16.5, 9.7 Hz, 1H). $^{19}$F{$^1$H} NMR (470 MHz, CDCl3, 294K): δ −60.27 (s, 3F). $^{31}$P{$^1$H} NMR (202 MHz, CDCl$_3$, 294K): δ 6.29 (d, J=11.1 Hz, 1P), 6.18 (d, J=11.1 Hz, 1P).

Example 5b

Ir(bdpp)$_2$(fpbpz) (5b)

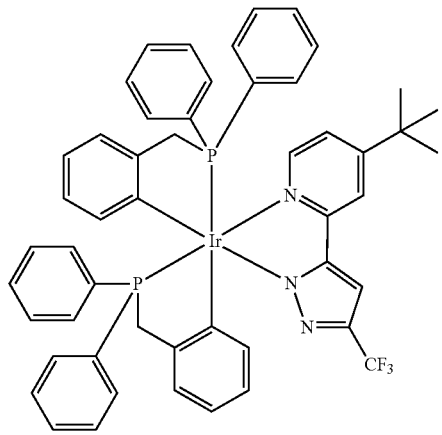

The synthesis procedures of complex 5b is similar with that of 5a except the fppzH was replaced by fpbpzH (168 mg, 0.6 mmol) and the yield of 5b is 32%.

Spectral data of 5b: MS (FAB, $^{192}$Ir), 1012 [M+1$^+$]. $^1$H NMR (500 MHz, CDCl$_3$, 294K): δ 7.94 (d, J=8.0 Hz, 1H), 7.92 (d, J=8.0 Hz, 1H), 7.44 (t, J=8.8 Hz, 2H), 7.35 (dd, J=6.3, 2.8 Hz, 1H), 7.31-7.26 (m, 2H), 7.20-7.07 (m, 8H), 6.95 (t, J=7.5 Hz, 2H), 6.86 (t, J=7.5 Hz, 1H), 6.81-6.78 (m, 4H), 6.73 (t, J=7.5 Hz, 1H), 6.70-6.64 (m, 3H), 6.58 (t, J=8.5 Hz, 2H), 6.45 (t, J=6.0 Hz, 1H), 6.32 (t, J=8.5 Hz, 2H), 6.21 (t, J=6.0 Hz, 1H), 4.23 (dd, J=14.5, 8.8 Hz, 1H), 3.74 (dd, J=14.5, 8.8 Hz, 1H), 3.44 (dd, J=16.5, 10.0 Hz, 1H), 2.09 (dd, J=16.5, 10.0 Hz, 1H), 1.17 (s, 9H). $^{19}$P{$^1$H} NMR (470 MHz, CDCl$_3$, 294K): δ −60.21 (s, 3F). $^{31}$P{$^1$H} NMR (202 MHz, CDCl$_3$, 294K): δ 6.38 (d, J=7.5 Hz, 1P), 6.18 (d, J=7.5 Hz, 1P).

Preparation Examples 6-8

Synthesis of Non-Conjugated C^C Ligand Bromide

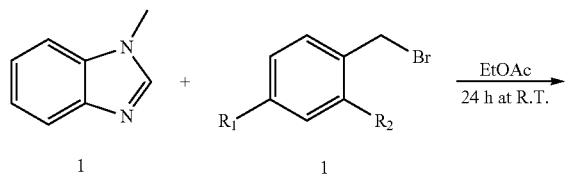

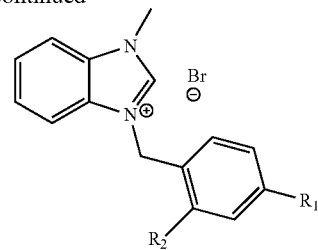

bmbH$_2$Br (R$^1$ = H, R$^2$ = H) 47%
dfbmbH$_2$Br (R$^1$ = F, R$^2$ = F) 73%
fbmbH$_2$Br (R$^1$ = F, R$^2$ = H) 81%

Preparation Example 6 bmbH$_2$Br 1-methylbenzimidazol (0.322 g, 2.43 mmol) and benzyl bromide (0.417 g, 2.43 mmol) were stirred in EtOAc (8 mL) at room temperature for 24 h. The precipitate was collected by filtration and dried in vacuum. The product was obtained as white solid in 47% yield (0.344 g, 1.14 mmol).

Spectra data of bmbH$_2$Br: $^1$H NMR (400 MHz, d$_6$-DMSO, 298 K): δ 9.84 (s, 1H), 8.02 (d, 2H, J$_{HH}$=8.4 Hz), 7.94 (d, 2H, J$_{HH}$=8.4 Hz), 7.64~7.70 (m, 2H), 7.50 (d, 2H, J$_{HH}$=7.2 Hz), 7.42~7.36 (m, 3H), 5.77 (s, 2H), 4.09 (s, 3H).

Preparation Example 7 dfbmbH$_2$Br dfbmbH$_2$Br was obtained in 73% by the similar procedure described for bmbH$_2$Br.

Spectra data of dfbmbH$_2$Br: $^1$H NMR (400 MHz, d$_6$-DMSO, 298 K): δ 9.83 (s, 1H), 8.04~7.99 (m, 2H), 7.77~7.68 (m, 3H), 7.41~7.36 (m, 1H), 7.18 (ddd, 1H, J$_{HF}$=8.60, J$_{HH}$=8.4, 2.4 Hz), 5.82 (s, 2H, CH$_2$), 4.09 (s, 3H, Me).

Preparation Example 8 fbmbH$_2$Br fbmbH$_2$Br was obtained in 81% by the similar procedure described for bmbH$_2$Br.

Spectra data of fbmbH$_2$Br: $^1$H NMR (400 MHz, d$_6$-DMSO, 298 K): δ 9.81 (s, 1H), 8.02 (dd, 1H, J$_{HH}$=7.2, 1.6 Hz), 7.95 (dd, 1H, J$_{HH}$=7.2, 1.6 Hz), 7.70~7.63 (m, 2H), 7.60~7.57 (m, 2H), 7.28~7.23 (m, 2H), 5.75 (s, 2H), 4.08 (s, 3H).

Preparation Examples 9-11

Synthesis of Non-Conjugated C^C Ligand

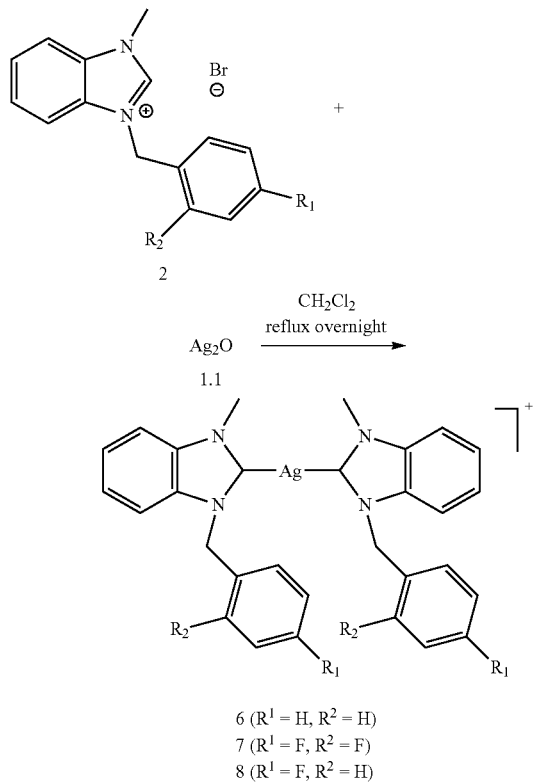

6 (R$^1$ = H, R$^2$ = H)
7 (R$^1$ = F, R$^2$ = F)
8 (R$^1$ = F, R$^2$ = H)

Preparation Example 9

Bis(3-benzyl-1-methyl-benzimidazolin-2-ylidene) silver bromide (6)

A 50 mL round-bottom flask was charged with silver (1) oxide (80 mg, 0.35 mmol), bmbH$_2$Br (70 mg, 0.323 mmol) and 20 mL of CH$_2$Cl$_2$. The reaction mixture was stirred and refluxed overnight under nitrogen while protected from light with aluminum foil. The reaction mixture was cooled to ambient temperature. Flash column chromatography on celite using CH$_2$Cl$_2$ as eluent was performed to remove the silver (I) salt. A colorless solution was obtained and concentrated. The product was obtained as white solid in 69% yield (50 mg, 0.079 mmol).

Spectra data of 6: MS (FAB): 553 (M). $^1$H NMR (400 MHz, d$_6$-DMSO, 298 K): δ 7.46~7.33 (m, 8H), 7.71 (d, 2H, J$_{HH}$=8 Hz), 7.77 (d, 2H, J=7.6 Hz), 7.32~7.25 (m, 6H), 5.71 (s, 4H), 4.05 (s, 6H).

Preparation Example 10

Bis(3-(2,4-difluorobenzyl)-1-methyl benzimidazolin-2-ylidene) silver bromide (7)

Ligand 7 was obtained in 83% by the similar procedure described for ligand 6.

Spectra data of 7: $^1$H NMR (400 MHz, d$_6$-DMSO, 298 K): δ 7.76 (d, 2H, J$_{HH}$=7.2 Hz), 7.72 (d, 2H, J$_{HH}$=7.2 Hz), 7.48~7.37 (m, 6H), 7.31~7.26 (m, 2H), 7.03 (ddd, 2H, J$_{HH}$=8.0, 2.4, J$_{HF}$=8.4 Hz), 5.71 (s, 4H), 4.06 (s, 6H).

Preparation Example 11

Bis(3-(4-difluorobenzyl)-1-methyl benzimidazolin-2-ylidene) silver bromide (8)

Ligand 8 was obtained in 84% by the similar procedure described for ligand 6.

Spectra data of 8: $^1$H NMR (400 MHz, d$_6$-DMSO, 298 K): δ 7.77 (d, 2H, J$_{HH}$=7.2 Hz), 7.72 (d, 2H, J=7.2 Hz), 7.44~7.40 (m, 8H), 7.17~7.13 (m, 4H), 5.70 (s, 4H), 4.05 (s, 6H).

Example 6a-8b

Synthesis of Ir(C^C)$_2$LX

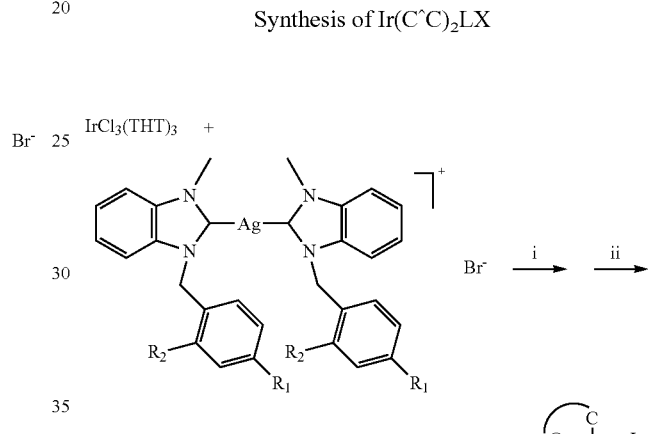

i. Reflux or stir at 130° C. in xylenes for 24 h
ii. Addition of ligand and Na$_2$CO$_3$, reflux or stir at 130° C. for 24 h

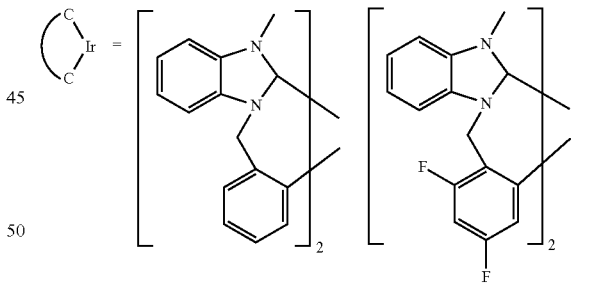

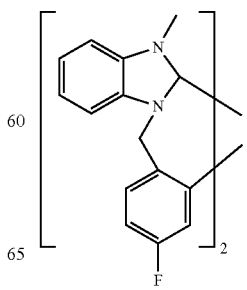

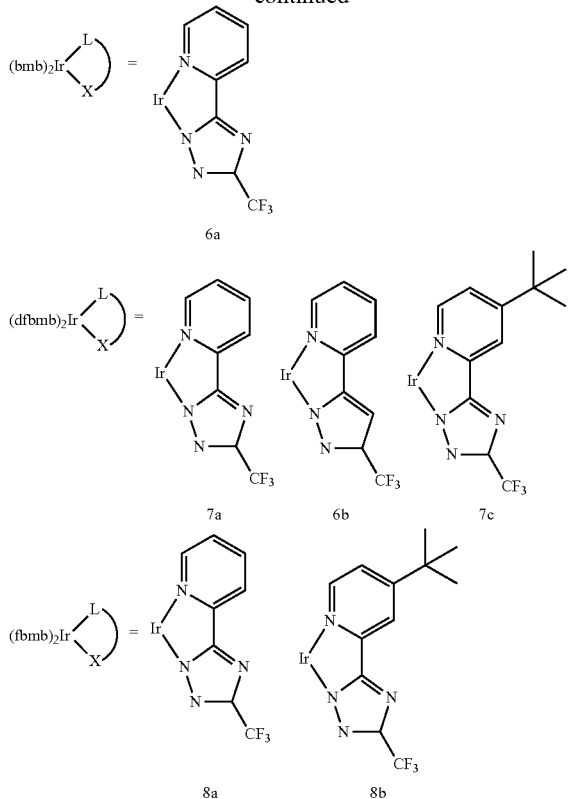

Example 6a

[Ir(bmb)₂(fptz)] (6a)

A xylene solution (20 mL) of IrCl₃(THT)₃ (70 mg, 0.125 mmol) and [(bmbH)₂Ag].Br (102 mg, 0.125 mmol) was heated at 130° C. for 12 h. After cooling to room temperature, bptzH (28.3 mg, 0.125 mmol) and Na₂CO₃ (0.132 g, 1.25 mmol) were added and this mixture was heated at 130° C. for another 24 h. Solution was concentrated under reduced pressure. Flash column chromatography on celite using CH₂Cl₂ as the eluent was performed to remove the insoluble materials. After removing solvent, the residue was purified by column chromatography eluting with CH₂Cl₂, and recrystallized from CH₂Cl₂/hexane to give yellow solid in 12% yield (12 mg, 0.014 mmol).

Spectra data of compound 6a: MS (FAB), 848 (M₊). ¹H NMR (400 MHz, CDCl₃, 298 K): δ 9.54 (d, 1H, $J_{HH}$=6.4 Hz), 8.05 (d, 1H, $J_{HH}$=7.6 Hz), 7.73 (t, 1H, $J_{HH}$=7.6 Hz), 7.44 (d, 1H, $J_{HH}$=8.4 Hz), 5.56 (d, 1H, $J_{HH}$=8.4 Hz), 7.29~7.25 (m, 3H), 7.22~7.11 (m, 6H), 6.98~6.91 (m, 2H), 6.76 (t, 1H, $J_{HH}$=7.2 Hz), 6.51 (t, 1H, $J_{HH}$=-7.2 Hz), 6.31 (d, 1H, $J_{HH}$=7.2 Hz), 6.27 (t, 1H, $J_{HH}$=7.2 Hz), 5.69 (d, 1H, $J_{HH}$=7.6 Hz), 5.57 (d, 1H, $J_{HH}$=15 Hz), 5.39 (d, 1H, $J_{HH}$=16 Hz), 5.25 (d, 1H, $J_{HH}$=15 Hz), 3.30 (s, 3H), 3.25 (s, 3H).

Example 7a

[Ir(dfbmb)₂(fptz)] (7a)

Compound 7a was obtained in 49% by the similar procedure described for compound 6a. The reaction temperature was changed from 130° C. to reflux. Purification was conducted by silica gel column chromatography using CH₂Cl₂/hexane (2:1) as eluent.

Spectra data of compound 7a: MS (FAB), 921 (M⁺), 707 (M⁺-fptz). ¹H NMR (500 MHz, d₆-acetone, 298 K): δ 9.42 (d, 1H, $J_{HH}$=5.5 Hz), 8.03 (td, 1H, $J_{HH}$=7.8, 1.5 Hz), 7.96 (d, 1H, $J_{HH}$=7 Hz), 7.89 (d, 1H, $J_{HH}$=8.0 Hz), 7.79 (d, 1H, $J_{HH}$=8.0 Hz), 7.61 (td, 1H, $J_{HH}$ 7.8, 1.5 Hz), 7.44 (d, 2H, $J_{HH}$=8.0 Hz), 7.39~7.33 (m, 2H), 7.28 (t, 2H, $J_{HH}$=8.0 Hz), 6.73 (d, 1H, $^2J_{HH}$=15.0 Hz), 6.56 (td, 1H, $J_{HH}$=10.5, $J_{HH}$=3.0 Hz), 6.41 (td, 1H, $J_{HF}$=10.5, $J_{HH}$=3.0 Hz), 6.12 (d, 1H, $^2J_{HH}$=16.5 Hz), 5.99 (d, 1H, $^2J_{HH}$=15.0 Hz), 5.75 (dd, 1H, $J_{HF}$=10.8, $J_{HH}$=2.0 Hz), 5.46 (d, 1H, $^2J_{HH}$=16.5 Hz), 5.23 (dd, 1H, $J_{HF}$=10.8, $J_{HH}$=2.0 Hz), 3.47 (s, 3H, Me), 3.38 (s, 3H, Me). ¹⁹F NMR (470 MHz, d₆-acetone, 298 K): δ −64.0 (s, 3F), −115.5 (s, 1F), −117.0 (s, 1F), −117.8 (s, 1F), −118.4 (s, 1F).

Example 7b

[Ir(dfbmb)₂(bppz)] (7b)

Compound 7b was obtained in 32% by the similar procedure described for compound 6a. But the temperature of the reaction was changed from 130° C. to reflux. Purification was conducted by silica gel column chromatography using CH₂Cl₂/hexane (2:3) as eluent.

Spectra data of compound 7b: MS (FAB), 976 (M⁺), 707 (M⁺-bppz). ¹H NMR (400 MHz, d₆-acetone, 298 K): δ 9.16 (d, 1H, $J_{HH}$=6.4 Hz), 7.87 (d, 1H, $J_{HH}$=8.4 Hz), 7.81~7.77 (m, 2H), 7.44~7.42 (m, 3H), 7.38~7.32 (m, 2H), 7.29~7.24 (m, 2H), 7.03~7.00 (m, 2H), 6.53 (td, 1H $J_{HF}$=11.2, 3.2 Hz), 6.37 (td, 1H $J_{HF}$=10.4, $J_{HH}$=2.8 Hz), 6.08 (d, 1H, $J_{HH}$=16 Hz), 5.93 (d, 1H, $J_{HH}$=14.4 Hz), 5.72 (d, 1H, $J_{HF}$=10.4 Hz), 5.43 (d, 1H, $J_{HH}$=16 Hz), 5.22 (d, 1H, $J_{HF}$=10.8 Hz), 3.44 (s, 3H), 3.38 (s, 3H), 1.31 (s, 914). ¹⁹F NMR (470 MHz, d₆-acetone, 298 K): δ −118.8 (s, 1F), −118.3 (s, 1F), −117.3 (s, 1F), −116.0 (s, 1F), −60.5 (s, 3F).

Example 7c

[Ir(dfbmb)₂(bptz)] (7c)

Compound 7e was obtained in 45% by the similar procedure described for Compound 6a. But the temperature of the reaction was changed from 130° C. to reflux. Purification was conducted by silica gel column chromatography using CH₂Cl₂/hexane (3:2) as eluent.

Spectra data of compound 7c: MS (FAB): 977 (M⁺), 707 (M⁺-bptz). ¹H NMR (400 MHz, d₆-acetone, 298 K): δ 9.27 (d, 1H, $J_{HH}$=6 Hz), 7.93 (d, 1H, $J_{HH}$=1.6 Hz), 7.89 (d, 1H, $J_{HH}$ 8.4 Hz), 7.80 (d, 111, $J_{HH}$=7.6 Hz), 7.64 (dd, 1H, $J_{HH}$=6.0, 2.4 Hz), 7.45 (t, 2H, $J_{HH}$=7.8 Hz), 7.39~7.34 (m, 2H), 7.31~7.26 (m, 2H), 6.67 (d, 1H, $J_{HH}$=15 Hz), 6.57 (td, 1H, $J_{HH}$=10.8, $J_{HH}$=2.8 Hz), 6.41 (td, 1H, $J_{HF}$=10.4, $J_{HH}$=2.4 Hz), 6.12 (d, 1H, $J_{HH}$=16 Hz), 5.98 (d, 1H, $J_{HH}$=15 Hz), 5.75 (d, 1H, $J_{HF}$=12.8 Hz), 5.44 (d, 1H, $J_{HH}$=16 Hz), 5.23 (d, 1H, $J_{HF}$=10.4 Hz), 3.44 (s, 3H), 3.39 (s, 3H), 1.33 (s, 9H). ¹⁹F NMR (470 MHz, d₆-acetone, 298 K): δ −118.4 (s, 1F), −117.8 (s, 1F), −117.0 (s, 1F), −115.7 (s, 1F), −63.9 (s, 3F).

Example 8a

[Ir(fbmb)₂(fptz)] (8a)

Compound 8a was obtained in 36% by the similar procedure described for Compound 6a. Purification was conducted by silica gel column chromatography using CH₂Cl₂/hexane (1:1) as eluent.

Spectra data of compound 8a: MS (FAB): 884 (M+), 670 (M+-fptz). $^1$H NMR (400 MHz, d$_6$-acetone, 298 K): δ 9.33 (d, 1H, J=5.6 Hz), 8.01~7.97 (m, 2H), 7.87 (d, 1H, J=8 Hz), 7.77 (d, 1H, J=8 Hz), 7.59~7.56 (m, 1H), 7.44~7.41 (m, 3H), 7.35~7.22 (m, 5H), 6.98 (d, 1H, J=14.4 Hz), 6.64 (ddd, 1H, $J_{HF}$=9.0, $J_{HH}$=8.4, 2.8 Hz), 6.46 (ddd, 1H, $J_{HF}$=9.0, $J_{HH}$=8.4, 2.8 Hz), 5.91 (dd, 1H, $J_{HF}$=14.4 Hz, $J_{HH}$=2.8 Hz), 5.82~5.71 (m, 2H), 5.60 (d, 1H, J=14.4 Hz), 5.35 (dd, 1H, $J_{HF}$=14.4 Hz, $J_{HH}$=2.8 Hz), 3.45 (s, 3H, Me), 3.38 (s, 3H, Me).

Example 8b

[Ir(fbmb)$_2$(bppz)] (8b)

Compound 8b was obtained in 33% by the similar procedure described for Compound 6a. Purification was conducted by silica gel column chromatography using CH$_2$Cl$_2$ as eluent.

Spectra data of compound 8b: MS (FAB): 940 (M+), 670 (M+-bptz). $^1$H NMR (400 MHz, d$_6$-acetone, 298 K): δ 9.19 (d, 1H, $J_{HH}$=6.2 Hz), 7.93 (d, 1H, $^4J_{HH}$=2.4 Hz), 7.86 (d, 1H, $J_{HH}$=8.4 Hz), 7.76 (d, 1H, $J_{HH}$=8.4 Hz), 7.62 (dd, 1H, $J_{HH}$=6.2, 2.4 Hz), 7.44~7.39 (m, 3H), 7.34~7.21 (m, 5H), 6.96 (d, 1H, $^2J_{HH}$=14.4 Hz), 6.63 (ddd, 1H, $J_{HF}$=9.0, $J_{HH}$=8.4, 2.8 Hz), 6.45 (ddd, 1H, $J_{HF}$=9.0, $J_{HH}$=8.4, 2.8 Hz), 5.89 (dd, 1H, $J_{HF}$=14.4, $J_{HH}$=2.8 Hz), 5.81~5.70 (m, 2H), 5.59 (d, 1H, $^2J_{HH}$=14 Hz), 5.35 (dd, 1H, $J_{HF}$=14.4 Hz, $J_{HH}$=2.8 Hz), 3.39 (s, 3H, Me), 3.43 (s, 3H, Me), 1.33 (s, 9H). $^{19}$F NMR (470 MHz, CDCl$_3$, 298 K): δ −63.3 (s, 3F), −118.0 (s, 1F), −119.5 (s, 1F).

Selected photophysical data of complexes 1a-8b prepared in Examples 1a-8b, were measured in degassed CH$_2$Cl$_2$ solution at RT and are shown in Table 1.

TABLE 1

| | abs. $\lambda_{max}$/nm (ε × 10$^{-3}$) | em $\lambda_{max}$/nm | Φ (%) | $\tau_{obs}$/µs |
|---|---|---|---|---|
| 1a | 269 (21.2), 367 (1.3) | 435, 458 | 6 | 0.17 |
| 1b | 261 (23.0), 368 (1.8) | 460 | 10 | 0.10 |
| 1f | 276 (43.8), 343 (8.5) | 464, 488 | 45 | 2.77 |
| 1g | 267 (28.1), 340 (5.6) | 456, 480 | 20 | 1.23 |
| 2b | 261 (22.3), 287 (14.7), 371 (1.8) | 460 | 9 | 0.15 |
| 3b | 261 (24.0), 284 (16.1), 372 (1.4) | 460 | 11 | 0.08 |
| 4b | 261 (21.8), 284 (15.4), 370 (1.4) | 457 | 4 | 0.07 |
| 5a | 267 (23.5), 314 (8.7), 360 (1.6) | 462, 485 | — | — |
| 5b | 260 (29.5), 312 (9.7), 351 (2.2) | 427, 451 | — | — |
| 6a | 302 (30.4), 326 (20.7), 396 (1.2) | 499 | 60 | 0.78 |
| 7a | 293 (23.7), 316 (26.5), 363 (1.8) | 458 | 73 | 0.38 |
| 7b | 295 (29.6), 320 (31.5), 359 (2.5) | 450, 477 | 30 | 0.94 |
| 7c | 292 (45.9), 320 (36.7), 361 (5.9) | 434, 455 | 30 | 0.29 |
| 8a | 297 (35.2), 321 (30.2), 372 (2.0) | 509 | 35 | 0.48 |
| 8b | 298 (25.0), 322 (22.1), 363 (1.8) | 460 | 22 | 0.22 |

Example 12

[Ir(bdpp)(fppz)$_2$] (9)

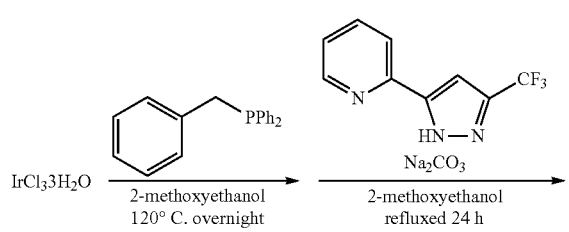

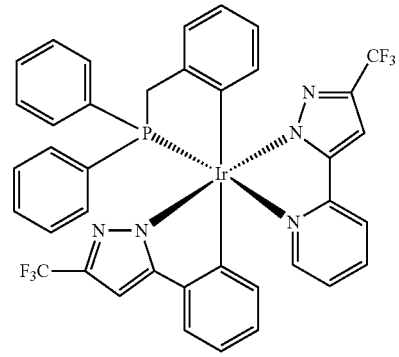

A mixture of IrCl$_3$·3H$_2$O (211 mg, 0.6 mmol) and benzyldiphenylphosphine (166 mg, 0.6 mmol) was dissolved in degassed 2-methoxyethanol and heated to 120° C. overnight, giving transparent yellow solution. After cooled to room temperature, fppzH (269 mg, 1.26 mmol) and Na$_2$CO$_3$ (636 mg, 6.0 mmol) was added into the solution. The reaction mixture was refluxed for another 24 h. After cooling to room temperature, reaction was quenched by addition of excess water. The resulting precipitate was collected by filtration and washed by ice MeOH, diethyl ether, then dried under vacuum. The product was purified by silica-gel column chromatography using EA/hexane (1:4) as eluent. Recrystallization in mixed CH$_2$Cl$_2$/hexane solution at room temperature gave xx as white powder (48 mg, 0.05 mmol, 8.4%).

Spectra data of 9. $^1$H NMR (500 MHz, CDCl$_3$, 294K): δ 7.70 (t, J=7.5 Hz, 1H), 7.63 (t, J=7.6 Hz, 1H), 7.53 (d, J=8.0 Hz, 2H), 7.37-7.32 (m, 4H), 7.18 (t, J=7.8 Hz, 2H), 7.15-7.13 (m, 1H), 7.10-7.05 (m, 2H), 6.97-6.95 (m, 4H), 6.88-6.77 (m, 5H), 6.75 (s, 1H), 6.72 (s, 1H), 4.99 (t, J=13.5 Hz, 1H), 3.65 (t, J=14.0 Hz, 1H). $^{19}$F{$^1$H} NMR (470 MHz, CDCl$_3$, 294K): δ −60.37 (s, 3F), −60.66 (s, 3F). $^{31}$P{$^1$H} NMR (202 MHz, CDCl$_3$, 294K): δ 11.53 (s, 1P).

Example 13

[Ir(dfbmb)(fptz)$_2$] (10)

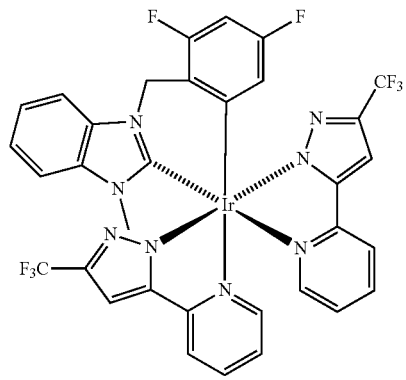

A mixture of 3-trifluoromethyl-5-(2-pyridyl) pyrazole (fppzH) (0.13 g, 0.61 mmol) and IrCl$_3$·3H$_2$O (0.10 g, 0.29 mmol) in DGME (20 mL) was refluxed for 4 hours under N$_2$. The mixture was then cooled to room temperature, and 0.11 g (0.32 mmol) 1-(2,4-difluorobenzyl)-3-methyl-benzimidazolium bromide (dfbmbH$_2$Br) and 0.13 g (0.56 mmol) Ag$_2$O were added. The resulting mixture was refluxed for 12 hours, and 20 mL water was added after cooling the solution to RT and removing some DGME solvent, the yellow precipitate was collected by filtration. The precipitate was separated using silica gel column chromatography (CH$_2$Cl$_2$), giving a bright blue emissive complex (0.032 g, 0.037 mmol, 13%).

Spectral data of 10: MS (FAB, $^{192}$Ir): 874 [M$^+$+1]. $^1$H NMR (400 MHz, d$_6$-acetone, 294 K): δ 8.18 (d, J$_{HH}$=8.0 Hz, 1H), 8.04~7.95 (m, 3H), 7.85 (d, J$_{HH}$=7.5 Hz, 1H), 7.63 (s, 1H), 7.52 (d, J=8.5 Hz, 1H), 7.38~7.35 (m, 2H), 7.32~7.27 (m, 2H), 7.23 (t, J$_{HH}$=6.0 Hz, 1H), 7.20 (s, 1H), 7.10 (d, J$_{HH}$=5.5 Hz, 1H), 6.44 (td, J$_{HH}$=9.5, 2.0 Hz, 1H), 6.17 (d, J$_{HH}$=15.0 Hz, 1H), 5.94 (s, 1H, br), 5.86 (d, J$_{HH}$=14.5 Hz, 1H), 3.66 (s, 3H). $^{19}$F NMR (470 MHz, d$_6$-acetone, 294 K): δ −118.9 (s, 1F), −117.3 (s, 1F), −60.9 (s, 3F), −60.8 (s, 3F). Anal. Calcd. for C$_{33}$H$_{21}$F$_8$IrN$_8$: N, 12.82; C, 45.36; H, 2.42. Found: N, 12.03; C, 45.45; H, 2.02.

The invention claimed is:

1. A phosphorescent tris-chelated iridium metal complex comprising one non-conjugated cyclometalated ligand forming a coordination sphere thereof with iridium, and two ligated chromophores being incorporated into the coordination sphere, wherein the ligated chromophores possess a relatively lower energy gap in comparison with that of the non-conjugated cyclometalated ligand, the latter afforded an effective barrier for inhibiting the ligand-to-ligand charge transfer process, so that a subsequent radiative decay from an excited state of the phosphorescent tris-chelated iridium metal complex will be confined to the ligated chromophores, wherein the complex is represented by the following formula IIb and its stereo isomers:

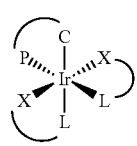

(IIb)

wherein the non-conjugated cyclometalated ligand is represented by P and C linked with an arch, and has a formula of Ar$_5$—C(R$_1$R$_2$)—P(Ar$_6$Ar$_7$), wherein Ar$_5$, Ar$_6$ and Ar$_7$ independently are an identical carbocyclic aromatic ring or different carbocyclic aromatic rings; R$_1$ and R$_2$ independently are H or methyl; and C in the formula IIb is a carbon atom contained in Ar$_5$, wherein the ligated chromophore is represented by the L and X linked with an arch, and has formula of Ar$_3$—Ar$_4$, wherein Ar$_3$ and Ar$_4$ independently are an aromatic ring or N-heterocyclic ring, or Ar$_3$—Ar$_4$ together are

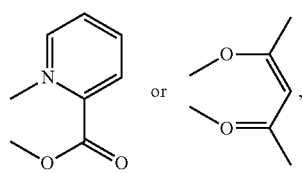

and wherein L is N or O, and X is C, N or O.

2. The complex of claim 1, wherein the energy gap of the ligated chromophore is for blue, green or red emission.

3. The complex of claim 1, wherein the non-conjugated cyclometalated ligands are

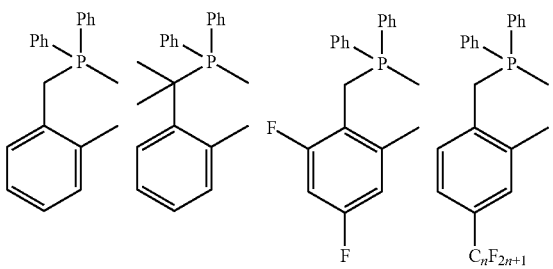

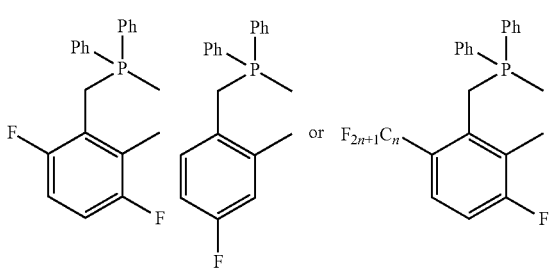

wherein Ph is phenyl, and n is an integer of 1-3.

4. The complex of claim 3, wherein positions of F and C$_n$F$_{2n+1}$ groups on phenyl rings of the non-conjugated cyclometalated ligands are varied, and n is 1.

5. The complex of claim 1, wherein the ligated chromophores are

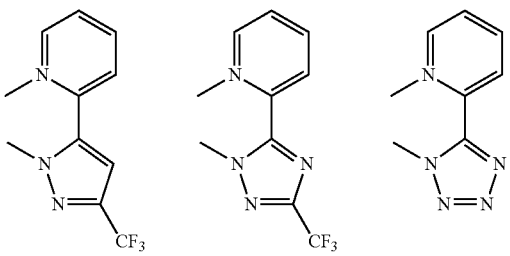

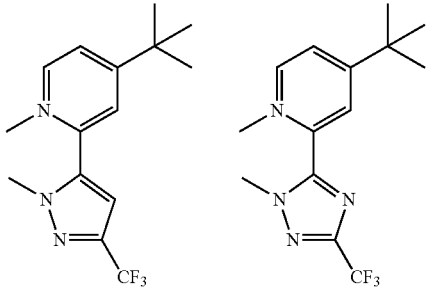

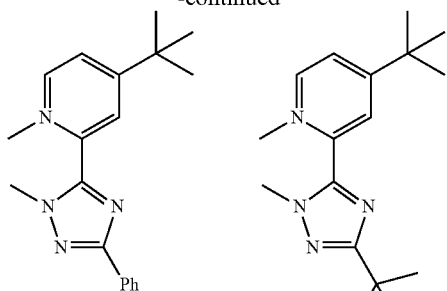
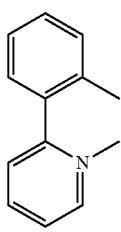
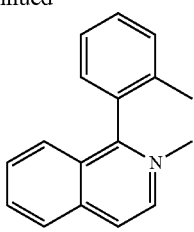
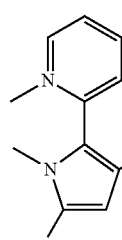
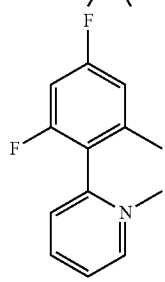
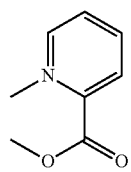 or 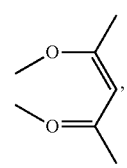
wherein Ph is phenyl.
* * * * *

UNITED STATES PATENT AND TRADEMARK OFFICE
CERTIFICATE OF CORRECTION

PATENT NO. : 8,592,585 B2
APPLICATION NO. : 13/219754
DATED : November 26, 2013
INVENTOR(S) : Yun Chi et al.

It is certified that error appears in the above-identified patent and that said Letters Patent is hereby corrected as shown below:

On the title page, item

"(73) Assignee: National Tsing Hua University
                 Hsinchu (TW)"

should read:

--(73) Assignee: E-Ray Optoelectronics Technology Co., Ltd.
                 Chung-Li (TW)--

Signed and Sealed this
First Day of April, 2014

Michelle K. Lee
*Deputy Director of the United States Patent and Trademark Office*